(12) United States Patent
Lu et al.

(10) Patent No.: US 11,136,333 B2
(45) Date of Patent: Oct. 5, 2021

(54) FUNCTIONALIZED PYRANO[2,3-D]PYRIMIDIN-7-ONE DERIVATIVES AND METHODS FOR THEIR PREPARATION AND USE

(71) Applicant: The Texas A&M University System, College Station, TX (US)

(72) Inventors: Dai Lu, Kingsville, TX (US); Chang-Jiang Qiao, Kingsville, TX (US); Boqiao Fu, Kingsville, TX (US); Anantha Lakshmi Duddupudi, Kingsville, TX (US); Zhixing Wu, Kingsville, TX (US)

(73) Assignee: The Texas A&M University System, College Station, TX (US)

( * ) Notice: Subject to any disclaimer, the term of this patent is extended or adjusted under 35 U.S.C. 154(b) by 76 days.

(21) Appl. No.: 16/304,073

(22) PCT Filed: May 23, 2017

(86) PCT No.: PCT/US2017/034082
§ 371 (c)(1),
(2) Date: Nov. 20, 2019

(87) PCT Pub. No.: WO2017/205432
PCT Pub. Date: Nov. 30, 2017

(65) Prior Publication Data
US 2019/0389874 A1 Dec. 26, 2019

Related U.S. Application Data

(60) Provisional application No. 62/340,393, filed on May 23, 2016, provisional application No. 62/508,958, filed on May 19, 2017.

(51) Int. Cl.
*C07D 471/04* (2006.01)
*A61K 31/519* (2006.01)
*C07D 491/052* (2006.01)

(52) U.S. Cl.
CPC .............................. *C07D 491/052* (2013.01)

(58) Field of Classification Search
CPC ........................... C07D 471/04; A61K 31/519
See application file for complete search history.

(56) References Cited

U.S. PATENT DOCUMENTS

| 7,244,727 | B2 | 7/2007 | Fox et al. |
| 2003/0073668 | A1 | 4/2003 | Booth et al. |
| 2006/0264489 | A1 | 11/2006 | Palani et al. |
| 2011/0257207 | A1 | 10/2011 | Backes et al. |

FOREIGN PATENT DOCUMENTS

| CN | 105481858 A | 4/2016 |
| EP | 1 364 950 A1 | 11/2003 |
| WO | 2010/071846 A2 | 6/2010 |

OTHER PUBLICATIONS

Kvita et al. ( Helvetica Chimica Acta (1988), 71(6), 1467-73). Abstarct.*
International Search Report and Written Opinion dated Aug. 29, 2017, issued in corresponding International Application No. PCT/US2017/34082, filed May 23, 2017, 10 pages.
PubChem Compound Summary for CID 68822568, "SCHEMBL3874380," U.S. National Library of Medicine, Nov. 30, 2012, <https://pubchem.ncbi.nlm.nih.gov/compound/68995121> [retrieved Jul. 24, 2017], 10 pages.

* cited by examiner

*Primary Examiner* — Bruck Kifle
(74) *Attorney, Agent, or Firm* — Christensen O'Connor Johnson Kindness PLLC

(57) ABSTRACT

Functionalized pyrano[2,3-d]pyrimidin-7-one derivatives, methods for making the derivatives, and methods of using the derivatives as protein kinase inhibitors.

17 Claims, 7 Drawing Sheets

8H-Pyrido[2,3-d]pyrimidin-7-one  Pyrano[2,3-d]pyrimidin-7-one

I  II

PD17399  PD180970

PD0332991 (Palbociclib)  FRAX597

Reagents and reaction condition: a) CH$_3$ONa/CH$_3$OH, rt, 1.5 h; b) Ac$_2$O, reflux, 40 mins; c) DBDMH, DMF, CH$_2$Cl$_2$, 12 hrs, rt; e) DMF, reflux; f) Pd$_2$(dba)$_3$, K$_3$PO$_4$, S-Phos, toluene, 100 °C, 20 hrs; g) m-CPBA, CH$_2$Cl$_2$, rt, 30 h; h) DMF, 110°C, 12 hrs; i) m-CPBA, DCM, 10 min; j) K$_2$CO$_3$, R-NH$_2$, 110°C.

Reagents and reaction condition: a) Pd₂(dba)₃, K₃PO₄, S-Phos, toluene, 95 °C, 4-5 h; b) m-CPBA, CH₂Cl₂, 2-3 h, rt; c) diglyme, 150 °C, 1h.

Reagents and reaction conditions: i) SO₂Cl₂, MeCN, reflux, 2h; j) Pd(PPh₃)₄, dioxane, HCl, 30 min; l) 2-butanol, TFA, reflux, overnight.

PD173955

FUNCTIONALIZED PYRANO[2,3-D]PYRIMIDIN-7-ONE DERIVATIVES AND METHODS FOR THEIR PREPARATION AND USE

CROSS-REFERENCE TO RELATED APPLICATIONS

This application claims the benefit of U.S. Application No. 62/340,393, filed May 23, 2016, and U.S. Application No. 62/508,958, filed May 19, 2017, each application expressly incorporated herein by reference in its entirety.

FIELD OF THE INVENTION

The present invention relates to functionalized pyrano[2,3-d]pyrimidin-7-one derivatives, to the preparation thereof and to the therapeutic use thereof, wherein said compounds are of general Formula (A). These compounds are potentially useful in treating disorders associated with aberrant protein kinase activities, including but not limited to, cancers, cardiovascular diseases, and certain central nervous system disorders.

BACKGROUND OF THE INVENTION

Pyrido[2,3-d]pyrimidin-7-one (I) (see FIG. 1) belongs to an important family of pharmacophores, the purine- and ATP-related templates, which typically contain pyrimidine rings. Pharmaceutical exploration of the purine- and ATP-related templates have led to the discoveries of a number of drugs, such as Abacavia, Gleevec, Tarceva, and Iressa, and a few drug candidates in clinical trials. The structure of the pyrido[2,3-d]pyrimidin-7-one (I) has been previously identified as a privileged pharmacophore for the inhibition of ATP-dependent kinases. The kinase inhibitors derived from this pharmacophore are represented by Parke-Davis (now Pfizer) compounds PD0332991, PD173955 and PD180970. PD173955 and PD180970 (FIG. 2) are two well-known Bcr-Abl inhibitors discovered following imatinib (Gleevec). They function as dual inhibitors of Src and Bcr-Abl, and can inhibit many imatinib (Gleevec)-resistant mutants of Bcr-Abl. PD0332991 is a selective inhibitor of cyclin dependent kinases (CDK) 4 and 6. It was recently proved by FDA and marketed as Palbociclib for the treatment of breast cancer. Notably, the structure of pyrido[2,3-d]pyrimidin-7-one 9 (I) was also proposed as a key pharmacophore for inhibiting other cyclin-dependent kinases (CDKs) such as the cyclin-dependent kinase 5 (CDK5) (V. Krystof, S. Uldrijan, Cyclin-dependent kinase inhibitors as anticancer drugs, *Current Drug Targets*, 11 (2010) 291-302; H. Galons, N. Oumata, L. Meijer, Cyclin-dependent kinase inhibitors: a survey of recent patent literature, *Expert Opinion on Therapeutic Patents*, 20 (2010) 377-404). CDK5 has been implicated in the pathological processes that contribute to neurodegeneration in Alzheimer's disease (AD) (L.-H. Tsai, M.-S. Lee, J. Cruz, Cdk5, a therapeutic target for Alzheimer's disease? Biochimica et Biophysica Acta (BBA)-Proteins and Proteomics, 1697 (2004) 137-142). Abnormal activation of CDK5 promotes hyperphosphorylation of the tau protein, a process well recognized as a key contributor in AD pathogenesis. Additionally, pyrido[2,3-d]pyrimidin-7-one (I) pharmacophore has led to discovery of some PAK (p21-activated kinases) inhibitors, such as FRAX597 (FIG. 2), which is a potent, ATP-competitive inhibitor of group I PAKs (Licciulli, J. Maksimoska, C. Zhou, S. Troutman, S. Kota, Q. Liu, S. Duron, D. Campbell, J. Chernoff, J. Field, FRAX597, a small molecule inhibitor of the p21-activated kinases, inhibits tumorigenesis of neurofibromatosis type 2 (NF2)-associated Schwannomas, Journal of Biological Chemistry, 288 (2013) 29105-29114). It has been suggested that PAK1 not only is involved in both cancer initiation and progression, but also plays a role in the pathology of Alzheimer's, Huntington's Disease, Neurofibromatosis, Autism, Schizophrenia, Fragile X mental retardations (J. V. Kichina, A. Goc, B. Al-Husein, P. R. Somanath, E. S. Kandel, PAK1 as a therapeutic target, *Expert Opinion on Therapeutic Targets*, 14 (2010) 703-725; and H. Maruta, PAKs, RAC/CDC42 (p21)-activated Kinases: Towards the Cure of Cancer and Other PAK-dependent Diseases, Newnes, 2013).

The synthesis of pyrido[2,3-d]pyrimidin-7-one analogs typically requires fairly expensive starting materials that contains a pyrimidine ring, and often involves a tedious synthesis to build the pyridopyrimidinone core. Interestingly, the pharmacophore pyrano[2,3-d]pyrimidin-7-one (II) (see FIG. 1), which is a close structure of (I), has not yet been extensively studied in synthetic chemistry and pharmacology. Only a few syntheses of the pyrano[2,3-d]pyrimidin-7-one ring system have been reported. Most of these syntheses employed functionalized pyrimidines or barbituric acid analogs as starting materials, which in most cases led to pyrano[2,3-d]pyrimidin-7-one derivatives difficult to structurally modify for subsequent pharmaceutical applications. Presumably within the structure of pyrano[2,3-d]pyrimidin-7-one (II), the 2- and 6-positions are pharmacologically important as was implicated by the class of pyrido[2,3-d]pyrimidin-7-one (I) analogs.

Despite the advance noted above, there exists a need for new pyrido[2,3-d]pyrimidin-7-one analogs and methods for their preparation. The present invention seeks to fulfill these needs and provides further related advantages.

SUMMARY OF THE INVENTION

The present invention relates to pyrano[2,3-d]pyrimidin-7-one compounds, processes for preparing said compounds and the intermediates thereof, pharmaceutical compositions comprising said compounds, and methods of their use.

In one aspect, provided herein is a pyrano[2,3-d]pyrimidin-7-one compound having the structure of Formula (A):

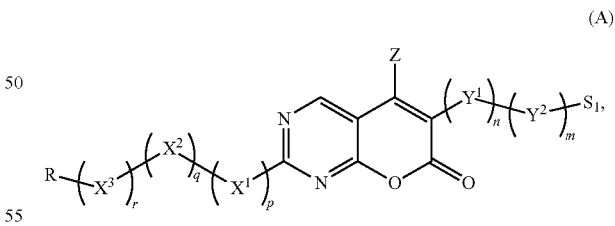

(A)

or a pharmaceutically acceptable salt, hydrate, or solvate thereof, wherein:

Z is selected from the group consisting of hydrogen, halogen, C(halogen)$_3$, a C$_1$-C$_6$ alkyl, and C$_3$-C$_6$ cycloalkyl;

X$^1$ is selected from the group consisting of NH$_2$, NR$^1$, O, and S, provided when X$^1$ is O, R—(X$^3$)$_r$—(X$^2$)$_q$— is not methyl;

R$^1$ is selected from the group consisting of hydrogen, C$_1$-C$_6$ alkyl, and C$_3$-C$_6$ cycloalkyl;

$X^2$ is an optionally substituted aryl or optionally substituted heteroaryl;

$X^3$ is an optionally substituted heterocyclyl;

R is H or alkyl;

$Y^1$ is O or an optionally substituted group selected from the group consisting of an aryl, a heteroaryl, an alkenyl, an alkynyl, and an acyl group;

$Y^2$ is an optionally substituted heteroaryl;

$S^1$ is hydrogen, halogen, alkyl, alkoxyl, cycloalkyl, cyano, OH, $SQ^1$, acyl, haloalkyl, heteroaryl, C(halogen)$_3$, CN, C(=O)CH$_3$, NQ$^1$C(=O)Q$^2$, C(=O)NQ$^1$Q$^2$, N$_3$, NCS, NO$_2$, or NQ$^1$Q$^2$, wherein $Q^1$ and $Q^2$ are independently selected from hydrogen and alkyl;

m is 0 or 1;

n is 0 or 1;

p is 0 or 1;

q is 0 or 1; and r is 0 or 1.

In certain group of embodiments, the compound of formula (A) has the structure of Formula (A1):

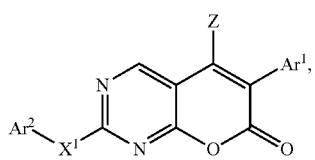

(A1)

or a pharmaceutically acceptable salt, hydrate, or solvate thereof, wherein:

Z is selected from the group consisting of hydrogen, halogen, CF$_3$, CCl$_3$, C$_1$-C$_6$ alkyl, and C$_3$-C$_6$ cycloalkyl;

$X^1$ is selected from the group consisting of NR$^1$, O, and S;

Ar$^1$ is an optionally substituted aryl or optionally substituted heteroaryl;

Ar$^2$ is an optionally substituted aryl or optionally substituted heteroaryl; and R$^1$ is hydrogen, C$_1$-C$_6$ alkyl or C$_3$-C$_6$ cycloalkyl.

In another aspect, provided herein are pharmaceutical compositions comprising pyrano[2,3-d]pyrimidin-7-one compounds of the present invention and a pharmaceutically acceptable carrier.

In an additional aspect, the invention provides a method of making 2 alkylsulfanylpyrano[2,3-d]pyrimidin-7-one comprising:

(i) contacting 2-alkylthiourea hemihydrate with a coumalate ester in a suitable solvent in the presence of a suitable base, thereby forming 3-(2-alkylsulfanyl-6-oxo-1,6-dihydro-pyrimidin-5-yl)acrylic acid; and (ii) contacting the 3-(2-alkylsulfanyl-6-oxo-1,6-dihydro-pyrimidin-5-yl)acrylic acid of step (i) with an anhydride thereby forming 2-alkylsulfanylpyrano[2,3-d]pyrimidin-7-one.

In yet another aspect, the invention provides a method of making 6-bromo-2-(methylthio)-7H-pyrano[2,3-d]pyrimidin-7-one comprising contacting 2-methylsulfanylpyrano[2,3-d]pyrimidin-7-one with 1,3-dibromo-5,5-dimethylhydantoin (DBDMH) in a suitable solvent wherein the contacting results in forming 6-bromo-2-(methylthio)-7H-pyrano[2,3-d]pyrimidin-7-one.

In another aspect, the invention provides a method for treating a disease or condition treatable by administering a protein kinase inhibitor, comprising administering to a subject in need thereof a therapeutically effective amount of a compound of the present invention.

Definitions

Unless otherwise stated, the following terms used in the present invention have the meanings given below.

The term "halogen" means a fluorine, a chlorine, a bromine or an iodine atom.

The term "halo" means fluoro, chloro, bromo, or iodo, preferably fluoro and chloro.

The term "alkyl group" means a saturated, linear or branched, aliphatic group. Examples of an alkyl group include the methyl, ethyl, n-propyl, n-butyl, n-pentyl, n-hexyl, n-heptyl, 1-methyl ethyl, 1-methylpropyl, 2-methylpropyl, 1,1-dimethyl ethyl, 1-methylbutyl, 2-methylbutyl, 3-methylbutyl, 1,1-dimethylpropyl, 1,2-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methyl-propyl, 1-ethyl-2-methylpropyl, 1-ethylbutyl, 2-ethylbutyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1,1,2,2-tetramethylpropyl, 1-ethylpentyl, 2-ethylpentyl, 3-ethylpentyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1-propylbutyl, 1-(1-methylethyl)butyl, and 1-(1-methylethyl)-2-methylpropyl groups.

The term "lower alkyl" means an alkyl group having 1 to 6 carbons linear or branched.

The term "alkenyl group" means a mono- or polyunsaturated, linear or branched, aliphatic group comprising, for example, one or two ethylenic unsaturations.

The term "alkynyl group" means a mono- or polyunsaturated, linear or branched, aliphatic group comprising, for example, one or two acetylenic unsaturations.

The term "cycloalkyl group" means cyclopropyl, cyclobutyl, cyclopentyl, cyclohexyl, cycloheptyl, bicyclo[2.2.1]heptyl, cyclooctyl, bicyclo[2.2.2]octyl, bicyclo[3.2.1]octyl or adamantyl.

The term "acyl" means a radical —C(O)R', where R' is hydrogen, alkyl, alkenyl, cycloalkyl, cycloalkylalkyl, phenyl or phenylalkyl wherein alkyl, cycloalkyl, cycloalkylalkyl, and phenyl-alkyl are as defined herein. Representative examples include, but are not limited to, formyl, acetyl, cylcohexylcarbonyl, cyclohexylmethylcarbonyl, benzoyl, benzylcarbonyl, and the like.

The term "alkoxyl" means a radical —OR where R is an alkyl as defined above. Representative examples include, but are not limited to methoxy, ethoxy, propoxy, butoxy, t-butoxyl and the like.

The term "aryl" means a monovalent monocyclic or polycyclic aromatic hydrocarbon radical; it includes, but is not limited to, phenyl and naphthyl.

The term "heteroaryl" means a monovalent monocyclic or bicyclic radical of 5 to 12 ring atoms having at least one aromatic ring containing one, two, or three ring heteroatoms independently selected from N, O, or S, the remaining ring atoms being C, with the understanding that the attachment point of the heteroaryl radical will be on an aromatic ring. More specifically, the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, and imidazo[2,1-b]thiazolyl.

The term "heterocyclic ring" or "heterocyclyl" means a saturated or unsaturated non-aromatic cyclic radical of 3 to 8 ring atoms in which one or two ring atoms are heteroatoms independently selected from N, O, or $S(O)_e$ (where e is an integer from 0 to 2). More specifically, the term heterocyclic ring includes, but is not limited to, tetrahydropyranyl, piperidino, N-methylpiperidin-3-yl, 2-oxo-piperidinyl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, pyrrolidinyl, imidazolinyl, and N-methanesulfonyl-piperidin-4-yl.

The term "substituent" (e.g., group $S^1$) means hydrogen, halogen, alkyl, alkoxyl, cycloalkyl, cyano, OH, $SQ^1$, acyl, haloalkyl, heteroaryl, C(halogen)$_3$, CN, C(=O)CH$_3$, $NQ^1$C(=O)$Q^2$, C(=O)$NQ^1Q^2$, $N_3$, NCS, $NO_2$, or $NQ^1Q^2$, wherein $Q^1$ and $Q^2$ are independently selected from H and alkyl.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
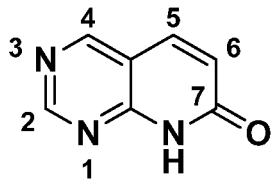
FIG. 1 illustrates the structures of pyrido[2,3-d]pyrimidin-7-one and pyrano[2,3-d]pyrimidin-7-one pharmacophores.
Figure 1:
Figure 2:
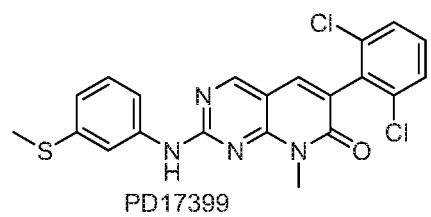
FIG. 2 illustrates the structures of protein kinase inhibitors PD173955, PD180970, PD0332991 (palbocicib) and FRAX597.
Figure 2:
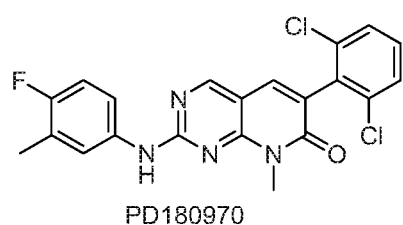
Figure 2:
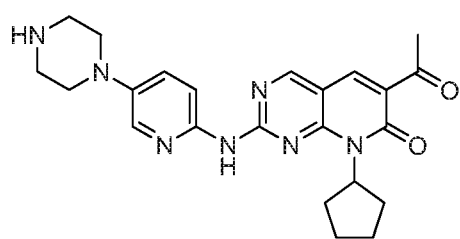
Figure 2:
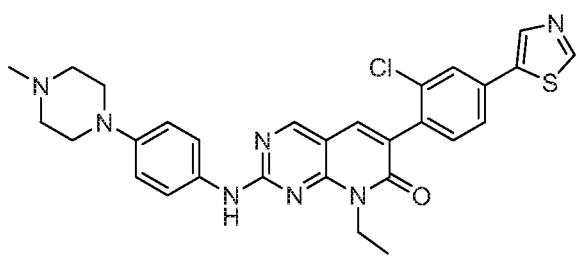

The present invention relates to functionalized pyrano[2,3-d]pyrimidin-7-one derivatives, to the preparation thereof and to the therapeutic use thereof, wherein said compounds are of general Formulae (A)-(A4). These compounds can interact with protein kinases, which include but are not limited to src-Abl, cyclin dependent kinases (CDKs), P21-activated kinases (PAKs), and mitogen-activated protein kinases (MAPK). Hence, they are potentially useful in treating disorders associated with aberrant protein kinase activities, including but not limited to, cancers, cardiovascular diseases, and certain central nervous system disorders.

In some embodiments, the compounds of Formulae (A)-(A4) are inhibitors of ABL kinases. The Abelson (ABL) family of protein kinases comprises cytoplasmic ABL1 and ABL2, which link diverse extracellular stimuli to signaling pathways that control cell growth, survival, invasion, adhesion and migration. Inhibition of ABLs has been implied in many types of hematopoietic malignancies and solid tumors. Increased ABL kinase activity has been reported in several types of invasive breast cancer and other solid tumors. PD173955 is a known potent ABL inhibitor developed from the scaffold pyrido[2,3-d]pyrimidine-7-one. The compounds of the present invention represent a new class of ABL inhibitors.

Compositions of Functionalized Pyrano[2,3-d]Pyrimidin-7-One Derivatives

In one group of embodiments, the invention provides compounds having the structure of Formula (A):

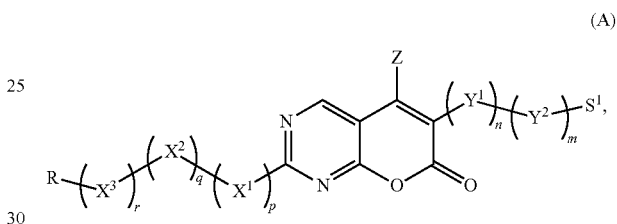

(A)

or a pharmaceutically acceptable salt, hydrate, or solvate thereof, wherein:

Z is hydrogen, halogen, C(halogen)$_3$, a lower alkyl, for example, $C_1$-$C_6$ alkyl, or lower cycloalkyl, for example, $C_3$-$C_6$ cycloalkyl;

$X^1$ is NH$_2$, NR$^1$, S, or O;

$R^1$ is hydrogen, a lower alkyl, for example, $C_1$-$C_6$ alkyl, or lower cycloalkyl, for example, $C_3$-$C_6$ cycloalkyl;

$X^2$ is an optionally substituted aryl or optionally substituted heteroaryl; wherein if said group is substituted, it is substituted independently with one or more substituents; preferably one or two substituents $S^1$;

$X^3$ is an optionally substituted heterocyclic ring; wherein if the heterocyclic ring is substituted, it is substituted independently with one or more substituents; preferably one or two substituents $S^1$;

R is hydrogen or an alkyl;

$Y^1$ is an optionally substituted group selected from an aryl, a heteroaryl, an alkenyl, an alkynyl, an acyl group, and oxygen; wherein if the said group is substituted, it is substituted independently with one or more substituents; preferably one or two substituents $S^1$;

$Y^2$ is an optionally substituted heteroaryl; wherein if the heteroaryl is substituted, it is substituted independently with one or more substituents; preferably one or two substituents and the substituents are as defined;

$S^1$ is hydrogen, halogen, alkyl, alkoxyl, cycloalkyl, cyano, OH, $SQ^1$, acyl, haloalkyl, heteroaryl, C(halogen)$_3$, CN, C(=O)CH$_3$, $NQ^1$C(=O)$Q^2$, C(=O)$NQ^1Q^2$, $N_3$, NCS, $NO_2$, or $NQ^1Q^2$, wherein $Q^1$ and $Q^2$ are independently selected from H and alkyl; and the subscripts m, n, p, q, and r are independently 0 or 1.

In certain embodiments of Formula (A), when $X^1$ is O, R—$(X^3)_r$—$(X^2)_q$—$(X^1)_p$— is not methyl. In other embodiments of Formula (A), when $X^1$ is O, R—$(X^3)_r$—$(X^2)_q$— is not methyl.

In a particular embodiment of Formula (A),
$X^1$ is NH where the subscript p is 1;
$X^2$ is a substituted aryl where the subscript q is 1;
the subscript r is 0;
$Y^1$ is a substituted aryl where the subscript n is 1;
the subscript m is 0.

In another particular embodiment of Formula (A),
$X^1$ is NH where the subscript p is 1;
$X^2$ is an optionally substituted aryl where the subscript q is 1;
$X^3$ is an optionally substituted heterocyclic ring where the subscript r is 1;
$Y^1$ is a substituted aryl where the subscript n is 1; and
the subscript m is 0.

In yet another particular embodiment of Formula (A),
$X^1$ is NH where the subscript p is 1;
$X^2$ is an optionally substituted heteroaryl where the subscript q is 1;
$X^3$ is an optionally substituted heterocyclic ring where the subscript r is 1;
$Y^1$ is a substituted aryl where the subscript n is 1; and
the subscript m is 0.

In a further particular embodiment of Formula (A),
$X^1$ is NH where the subscript p is 1;
$Y^1$ is an alkynyl where the subscript n is 1; and
the subscript m is 0.

In yet a further particular embodiment of Formula (A),
$X^1$ is NH where the subscript p is 1;
$Y^1$ is an acyl where the subscript n is 1; and
the subscript m is 0.

In another particular embodiment of Formula (A),
$X^1$ is NH where the subscript p is 1;
$Y^1$ is oxygen where the subscript n is 1; and
the subscript m is 0.

In a further particular embodiment of Formula (A),
$X^1$ is NH where the subscript p is 1;
$Y^1$ is optionally substituted aryl where the subscript n is 1; and
$Y^2$ is optionally substituted heteroaryl where the subscript m is 1.

In some embodiments of Formula (A), Z is selected from the group consisting of H, halogen, $CF_3$, $CCl_3$, $C_1$-$C_{10}$ alkyl, and $C_3$-$C_7$ cycloalkyl. Preferably, Z is H or F. In other embodiments of Formula (A), $S^1$ is hydrogen, halogen, alkyl, alkoxyl, cycloalkyl, cyano, OH, $SQ^1$, acyl, haloalkyl, heteroaryl, C(halogen)$_3$, CN, C(=O)$CH_3$, $NQ^1$C(=O)$Q^2$, C(=O)$NQ^1Q^2$, $N_3$, NCS, $NO_2$, or $NQ^1Q^2$, wherein $Q^1$ and $Q^2$ are independently selected from H and alkyl.

In a certain group of embodiments of the compounds of the present invention, the compound of Formula (A) has the structure of Formula (A1):

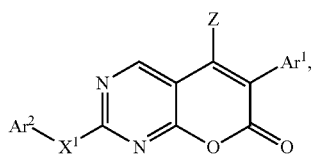

(A1)

or a pharmaceutically acceptable salt, hydrate, or solvate thereof,
wherein:
Z is selected from the group consisting of hydrogen, halogen, $CF_3$, $CCl_3$, $C_1$-$C_6$ alkyl, and $C_3$-$C_6$ cycloalkyl;
$X^1$ is selected from the group consisting of $NR^1$, O, and S;
$Ar^1$ is an optionally substituted aryl or optionally substituted heteroaryl;
$Ar^2$ is an optionally substituted aryl or optionally substituted heteroaryl; and
$R^1$ is H, $C_1$-$C_6$ alkyl or $C_3$-$C_6$ cycloalkyl.

In certain embodiments of Formula (A) or (A1), $X^1$ is $NR^1$, wherein $R^1$ is H or $C_1$-$C_6$ alkyl. In some embodiments of Formula (A1), $Ar^2$ is an optionally substituted phenyl, such as a mono- or di-substituted phenyl.

In some embodiments, the compound of Formula (A) or (A1) has the structure of Formula (A2):

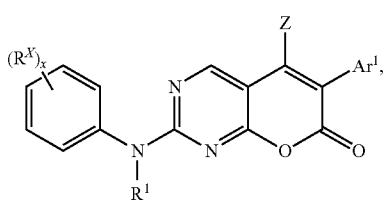

(A2)

or a pharmaceutically acceptable salt, hydrate, or solvate thereof,
wherein:
$R^X$ is hydrogen, halogen, alkyl, alkoxyl, cycloalkyl, cyano, OH, acyl, haloalkyl, heteroaryl, $SQ^1$, $CF_3$, $CCl_3$, CN, C(=O)$Q^1$, NHC(=O)$Q^2$, C(=O)$NQ^1Q^2$, $N_3$, NCS, $NO_2$, or $NQ^1Q^2$, wherein $Q^1$ and $Q^2$ are independently selected from H and $C_1$-$C_{10}$ alkyl;
Z, $Ar^1$, and $R^1$ are as defined for Formula (A1); and
x is 0, 1, 2, 3, 4, or 5.

In some embodiments of Formula (A2), $Ar^1$ is an optionally substituted phenyl, preferably, a mono- or di-substituted phenyl.

In particular embodiments, the compound of Formula (A), (A1), or (A2) has the structure of Formula (A3):

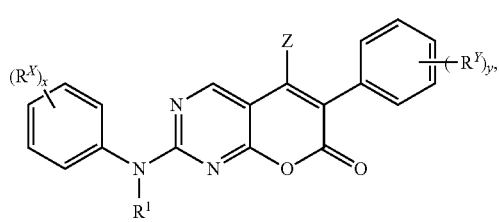

(A3)

or a pharmaceutically acceptable salt, hydrate, or solvate thereof,
wherein:
$R^Y$ is hydrogen, halogen, alkyl, alkoxyl, cycloalkyl, cyano, OH, acyl, haloalkyl, heteroaryl, $SQ^1$, $CF_3$, $CCl_3$, CN, C(=O)$Q^1$, NHC(=O)$Q^2$, C(=O)$NQ^1Q^2$, $N_3$, NCS, $NO_2$, or $NQ^1Q^2$, wherein $Q^1$ and $Q^2$ are independently selected from H and $C_1$-$C_{10}$ alkyl;
Z, $Ar^1$, $R^X$, x, and $R^1$ are as defined for Formula A2; and
y is 0, 1, 2, 3, 4, or 5.

In certain embodiments of Formula (A3), $R^1$ is H or methyl. Preferably, $R^1$ is H. In other embodiments of Formula (A3), Z is H, halogen, or methyl, or more preferably, Z is H.

In particular embodiments, the compound of Formula (A), (A1), (A2), or (A3) has the structure of Formula (A4):

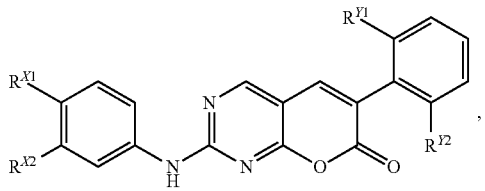

(A4)

or a pharmaceutically acceptable salt, hydrate, or solvate thereof,
wherein:
$R^{X1}$, $R^{X2}$, $R^{Y1}$, and $R^{Y2}$ are independently selected from the group consisting of hydrogen, halogen, alkyl, alkoxyl, cycloalkyl, cyano, OH, alkoxy, acyl, haloalkyl, heteroaryl, $SQ^1$, $CF_3$, $CCl_3$, CN, $C(=O)Q^1$, NHC$(=O)Q^1$, $C(=O)NQ^1Q^2$, $N_3$, NCS, $NO_2$, and $NQ^1Q^2$, wherein $Q^1$ and $Q^2$ are independently selected from H and $C_1$-$C_{10}$ alkyl.

In some embodiments of Formula (A4), $R^{Y1}$ and $R^{Y2}$ are independently selected from hydrogen, F, Cl, and $CH_3$. In other embodiments of Formula (A4), $R^{X1}$ is selected from hydrogen, F, Cl, $N(CH_3)_2$, and $CH_3$. In yet other embodiments of Formula (A4), $R^{X2}$ is selected from $NH_2$, $OCH_3$, CN, $SCH_3$, $NHC(O)CH_3$, and $CH_3$.

In some embodiments of the present invention, the compound of Formulae (A), (A1), (A2), (A3), or (A4) is a compound of Formulae 12a, 12b, 12c, 12d, 12e, 12f, 12g, 19a, or 19b of TABLE 1.

The activity of certain representative compounds of the present invention in comparison with the known ABL1 kinase inhibitor PD173955 is summarized in TABLE 1.

Methods for Making Functionalized Pyrano[2,3-d]Pyrimidin-7-One Derivatives

In one aspect, the present invention provides methods for making functionalized pyrano[2,3-d]pyrimidin-7-one derivatives.

In one embodiment, the invention provides a method for making a key intermediate, 2-methylsulfanylpyrano[2,3-d]pyrimidin-7-one (4), which is useful for making functionalized pyrano[2,3-d]pyrimidin-7-one derivatives.

The method of making 2-methylsulfanylpyrano[2,3-d]pyrimidin-7-one (Compound 4) is shown below in Scheme 1.

Scheme 1

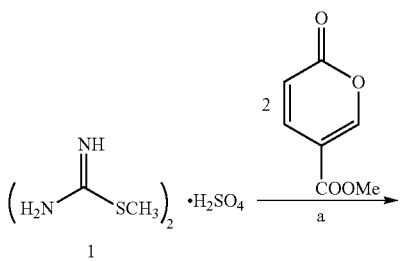

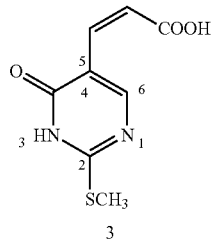

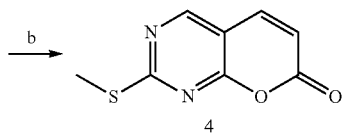

Reagents and reaction condition: a) $CH_3ONa/CH_3OH$, rt, 1.5 h; b) $Ac_2O$, reflux, 40 mins.

Figure 3:
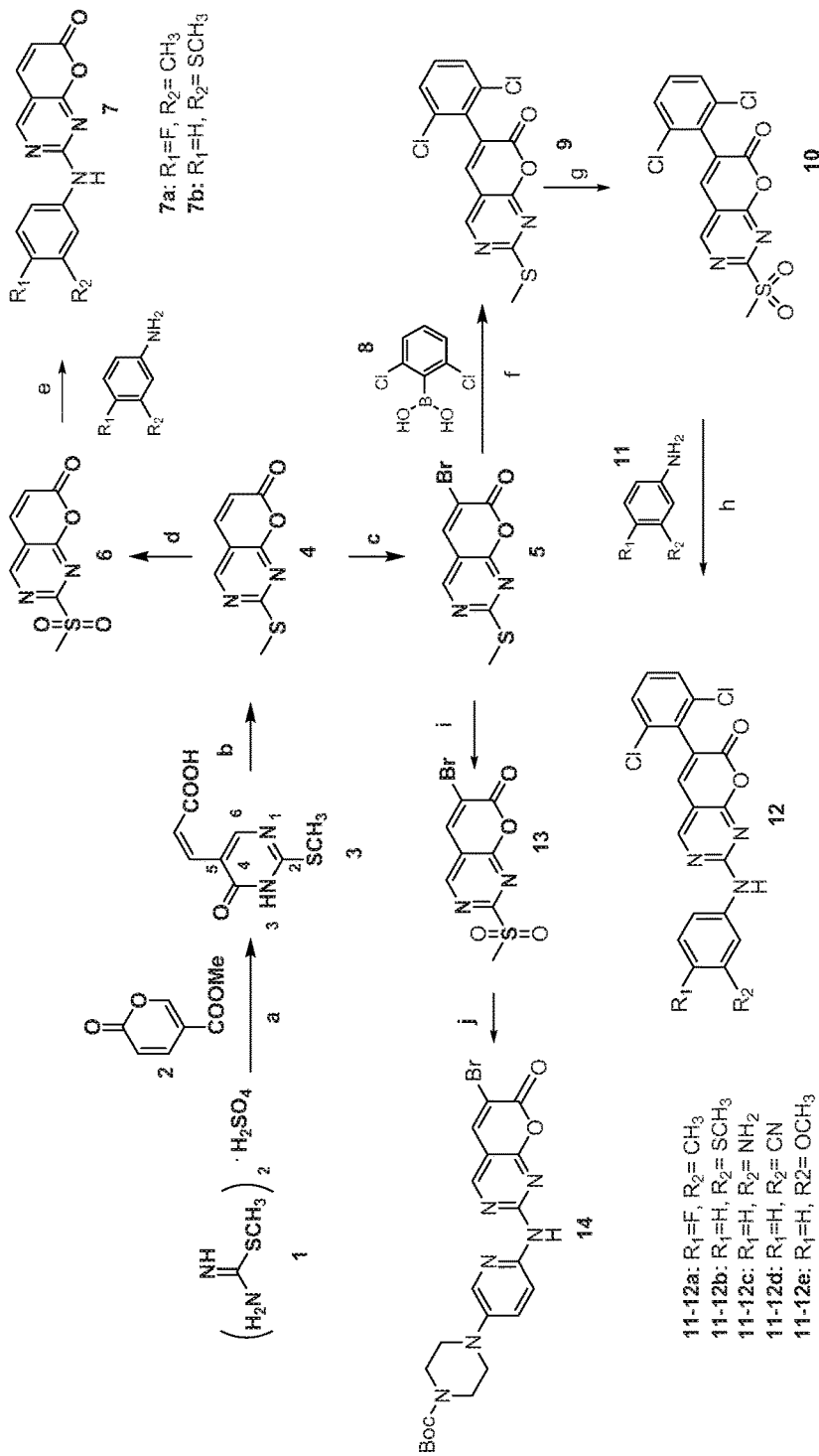
FIGS. 3, 4, and 5 are schematic illustrations of the synthesis of representative functionalized pyrano[2,3-d]pyrimidin-7-one derivatives of the invention.

Referring to Scheme 1, 2-alkylthiourea hemihydrate (1) is treated with a coumalate ester (2) under basic conditions (e.g., reaction conditions a: sodium methoxide in anhydrous methanol) to provide 3-(2-methylsulfanyl-6-oxo-1,6-dihydro-pyrimidin-5-yl)acrylic acid (3), which was converted to 2-methylsulfanylpyrano[2,3-d]pyrimidin-7-one (Compound 4) by treatment with an anhydride (e.g., reaction conditions b: acetic anhydride). A representative synthesis of Compound 4 is shown in FIG. 3 and described in Example 1.

In another embodiment, the invention provides a method for making a functionalized pyrano[2,3-d]pyrimidin-7-one derivative, 6-bromo-2-(methylthio)-7H-pyrano[2,3-d]pyrimidin-7-one (compound 5).

The method of making 6-bromo-2-(methylthio)-7H-pyrano[2,3-d]pyrimidin-7-one (compound 5) from 2-methylsulfanylpyrano[2,3-d]pyrimidin-7-one (Compound 4) is shown below in Scheme 2.

Scheme 2

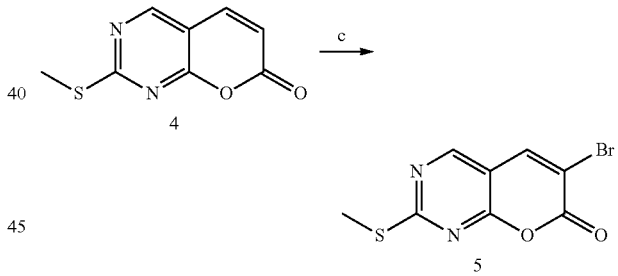

Reagents and reaction condition: c) 1,3-dibromo-5,5-dimethylhydantoin, DMF, rt, 70.5%.

Referring to Scheme 2, Compound 4 is treated with 1,3-dibromo-5,5-dimethylhydantoin (DBDMH) in dimethylformaldehyde (DMF) to provide 6-bromo-2-(methylthio)-7H-pyrano[2,3-d]pyrimidin-7-one (5).

In another embodiment, the present invention provides a facile synthesis of 6-bromo-2-methyl sulfanyl-pyrano[2,3-d]pyrimidin-7-one from 2-methyl-2-thiopseudourea and methyl coumalate. This dual functionalized pyranopyrimidin-7-one serves as a new chemical entity to provide a potentially useful building block for pharmaceutical applications.

In summary, a pyrano[2,3-d]pyrimidin-7-one template with a 2-$SCH_3$— and 6-bromo-functionality was prepared in three steps from easily accessible methyl coumalate and inexpensive 2-methyl-2-thiopseudourea. The 2-methylsulfanyl group allows for rapid and facile access to various substituents, such as amino analogs, alkyl ether derivatives, and other functional groups via chemistry that is well-developed in the class of pyrido[2,3-d]pyrimidin-7-one compounds. Additionally, the 6-bromo-functionality offers a gateway to a wide range of structural modifications via palladium-catalyzed coupling reactions, such as Suzuki coupling, Stille coupling, Heck reaction, and palladium-catalyzed C—N coupling reaction, that are very well-exemplified in the chemical classes of pyridopyrimidinones, chromen-2-ones and quinolin-2-ones. This new template, having dual sites for functionalization (e.g. 5), provides new opportunities for divergent syntheses in pharmaceutical applications as well as serve as a novel pharmacophore for the class of ATP- and purine-related pharmaceutical compounds.

It will be appreciated that the functionalized pyrano[2,3-d]pyrimidin-7-one derivatives of the invention can be provided in the form of a base or an acid addition salt prepare from a pharmaceutically acceptable salt including those known in the art, or in the form of a hydrate or solvate.

Methods for Using Functionalized Pyrano[2,3-d]Pyrimidin-7-One Derivatives

In a further aspect, the present invention provides methods for using functionalized pyrano[2,3-d]pyrimidin-7-one derivatives. The functionalized pyrano[2,3-d]pyrimidin-7-one derivatives described in Formula (A) can be used as therapeutic agents, such as protein kinase inhibitors.

The functionalized pyrano[2,3-d]pyrimidin-7-one derivatives of the invention can be used for the treatment of disorders associated with aberrant kinase activities, which include but are not limited to, cancers, cardiovascular diseases, and certain central nervous system disorders such as Alzheimer's, Huntington's Disease, neurofibromatosis, autism, schizophrenia, and fragile X mental retardations.

For therapeutic applications, the functionalized pyrano[2,3-d]pyrimidin-7-one derivatives of the invention can be formulated with a pharmaceutically acceptable carrier suitable for the desired method of administration. Pharmaceutically acceptable carriers are known in the art. The functionalized pyrano[2,3-d]pyrimidin-7-one derivatives of the invention can be administered systemically by oral, intravenous, subcutaneous, or topical administration.

The following examples are provided for the purpose of illustrating, not limiting the invention.

Example 1

The syntheses described below are illustrated in FIG. 3.

3-(2-Methyl sulfanyl-6-oxo-1,6-dihydro-pyrimidin-5-yl)-acrylic Acid (3)

To a solution of $CH_3ONa$ (5.26 g, 97.32 mmol) in anhydrous methanol (65 mL) was added 2-methyl-2-thiopseudourea hemisulfate 1 (13.5 g, 97.32 mmol). The reaction mixture was stirred at room temperature for 10 mins, and methyl coumalate (10.0 g, 64.88 mmol) was added. The reaction mixture was then stirred at room temperature for 1.5 h, and then concentrated in vacuo to remove the methanol. The residue was then dissolved and partitioned between chloroform (50 mL) and water (100 mL). The organic layer was separated and extracted with water (20 mL) two times. The combined aqueous extract was then treated with 12N aqueous HCl until pH 4 was reached. A light orange-colored solid precipitated and was filtered and washed three times with ice-cold water (15 mL) and three times with a acetone-hexane (1:1) mixture. The resulting solid was dried under vacuum to afford 7.49 g of 3 (54.3%). Mp: 208-209° C.; $^1H$ NMR ($d_6$-DMSO) δ 8.46 (s, 1H), 6.79 (d, J=12.6 Hz, 1H), 5.93 (d, J=12.6 Hz, 1H), 2.51 (s, 3H); MS m/z 211 ($M^+$−1). Elemental Analysis. ($C_8H_8N_2O_3S$) Calcd: C, 45.28%, H, 3.80%, N, 13.20%; Found: C, 45.13%, H, 3.75%, N, 12.88%.

2-Methylsulfanyl-pyrano[2,3-d]pyrimidin-7-one (4)

A suspension of 3 (7.0 g, 33 mmol) in acetic anhydride (40 mL) was refluxed for 40 mins. The reaction mixture then became homogeneous and was cooled to room temperature. Light greenish-colored crystals precipitated and were filtered and washed with ice-cooled acetic anhydride (10 mL) and diethyl ether two times (15 mL). The resulting crystals were then treated with a solution of sodium carbonate solution with stirring to remove the trace amount of impurity from uncyclized acids. The resulted solid was filtered and dried in vacuum to afford 4.5 g of 4 (70.4%). Mp: 178-179° C.; $^1H$ NMR ($d_6$-DMSO) δ 8.97 (s, 1H), 8.07 (d, J=9.6 Hz, 1H), 6.54 (d, J=9.6 Hz, 1H), 2.58 (s, 3H); MS m/z 195 ($M^+$+1). Elemental Analysis. ($C_8H_6N_2O_2S$) Calcd: C, 49.47%, H, 3.11%, N, 14.42%; Found: C, 49.55%, H, 3.19%, N, 14.35%.

6-Bromo-2-methylsulfanyl-pyrano[2,3-d]pyrimidin-7-one (5)

To a solution of 2-methylsulfanyl-pyrano[2,3-d]pyrimidin-7-one (4, 5.3 g, 27.2 mmol) in anhydrous DMF (42 mL) was added 1,3-dibromo-5,5-dimethyl-hydantoin (10.1 g, 35.4 mmol) in portions at room temperature. The resulting mixture was stirred at room temperature for 8 hours. The reaction mixture was slowly poured into a saturated aqueous $NaHSO_3$ solution (400 mL) and extracted with EtOAc (300 mL×3). The combined organic phases were washed with water, brine, dried over anhydrous $Na_2SO_4$, filtered and concentrated. The residue was recrystallized from DCM (20 mL) to give the titled product (4.9 g, 72.3%) as pale yellow crystals. $R_f$=0.56, hexane/EtOAc=3/2. mp: 174-175° C. $^1H$ NMR (300 MHz, DMSO-$d_6$) δ 8.92 (s, 1H), 8.58 (s, 1H), 2.58 (s, 3H); Elemental Analysis. ($C_8H_5BrN_2O_2S$) Calcd: C, 35.18%, H, 1.85%, N, 10.26%; Found: C, 35.30%, H, 1.69%, N, 10.23%.

2-Methylsulfonyl-pyrano[2,3-d]pyrimidin-7-one (6)

A suspension of 4 (97 mg, 0.5 mmol) in dichloromethane (5 mL) was stirred at room temperature for 10 mins until a homogenous solution resulted to which m-CPBA (246 mg, 1.1 mmol, 77% count) was then added. After stirring the reaction mixture for 16 h at room temperature, a white precipitate was formed and filtered (103 mg). This solid was washed with diethyl ether (1 mL) four times and acetone one time (1 mL) to afford 57 mg of 6 (50.4%). Mp: 180-182° C.; $^1H$ NMR ($d_6$-DMSO) δ 9.39 (s, 1H), 8.22 (d, J=9.6 Hz, 1H), 6.87 (d, J=9.6 Hz, 1H), 3.46 (s, 3H); MS m/z 226 ($M^+$); Elemental Analysis. ($C_8H_6N_2O_4S\cdot3H_2O$) Calcd: C, 34.29%, H, 4.32%, N, 10.00%; found: C, 34.35%, H, 4.38%, N, 9.95%.

2-(4-Fluoro-3-methylphenylamino)-7H-pyrano [2,3-d] pyrimidin-7-one (7a)

2-methyl-sulfonyl-pyrano [2, 3-d] pyrimidin-7-one (6, 0.2 g, 0.884 mmol) was taken in sealed tube and was added anhydrous diglyme (5.34 mL) under magnetic stirring. To this suspension 4-fluoro-methylaniline (0.243 g, 1.944 mmol) was added under room temperature. The reaction mixture was heated up to 162° C. for one hour and homogeneous solution was observed at 140° C. The reaction progress was monitored by TLC (80% ethyl acetate in hexane). After completion, reaction mixture was cooled to room temperature and mixed with water (40 mL), extracted with ethyl acetate for two times (35 mL). Combined organic layers were washed with water (40 mL) and brine (25 mL) and dried over anhydrous sodium sulfate. The organic layer was filtered and concentrated in vacuum to remove the solvent. The crude product was purified with Combiflash chromatography (0-80% ethyl acetate in hexane) and resulted 52 mg (21.75%) of 2-(4-fluoro-3-methylphenylamino)-7H-pyrano[2,3-d] pyrimidin-7-one as yellow solid. Mp: 233-234° C.; $^1$H NMR (d$_6$-DMSO) δ 2.24 (s, 3H), 6.27 (d, J=9.3 Hz, 1H), 7.12 (t, J=9.4 Hz, 1H), 7.58 (m, 2H), 7.97 (d, J=9.3 Hz, 1H), 8.82 (s, 1H), 10.32 (s, 1H); MS m/z 195 (M$^+$+1).

2-(3-(Methylthio)phenylamino)-7H-pyrano [2, 3-d] pyrimidin-7-one (7b)

2-methyl-sulfonyl-pyrano [2, 3-d] pyrimidin-7-one (6, 200 mg, 0.884 mmol) was taken in a sealed tube and was added anhydrous bis(2-methoxyethyl)ether (5.34 ml). To this magnetically stirred suspension, 3-(methylthio)aniline (270 mg, 1.944 mmol) was added dropwise at room temperature. The reaction mixture was stirred and heated to 162° C. for one hour. Homogeneous solution was observed at 120° C. Reaction progress was monitored by TLC (80% ethyl acetate in hexane). After completion, reaction mixture was cooled to room temperature; water (10 ml) was added and extracted twice with ethyl acetate (2×20 mL). The combined organic layers were washed with water (10 mL) and brine (15 mL). The organic layer was dried over anhydrous sodium sulfate, filtered and concentrated in vacuum to remove the solvent. The resulted crude product was purified with Combiflash chromatography (0-80% ethyl acetate in hexane) and provided 76 mg (31%) of 2-(3-(methylthio)phenylamino)-7H-pyrano[2,3-d]pyrimidin-7-one as light yellow solid. Mp: 201-203° C.; $^1$H NMR (d$_6$-DMSO) δ 2.48 (s, 3H), 6.30 (d, J=9.3 Hz, 1H), 6.95 (d, J=8.4 Hz, 1H), 7.29 (t, J=7.95 Hz, 1H), 7.56 (d, J=8.4 Hz, 1H), 7.73 (t, =1.5 Hz, 1H), 7.98 (d, J=9.3 Hz, 1H), 8.86 (s, 1H), 10.39 (s, 1H); MS m/z 285.32 (M$^+$+1).

6-(2,6-Dichlorophenyl)-2-(methylthio)-7H-pyrano [2,3-d]pyrimidin-7-one (9)

To a suspension of 2-dicyclohexylphosphino-2',6'-dimethoxybiphenyl (SPhos) (90 mg, 0.22 mmol), 2, 6-dichlorophenylboronic acid (314 mg, 1.65 mmol), K$_3$PO$_4$ (700.5 mg, 3.3 mmol) and Pd$_2$(dba)$_3$ (100.7 mg, 0.11 mmol) in 30 mL toluene, reaction mixture was degassed and 6-bromo-2-(methylthio)-7H-pyrano[2,3-d]pyrimidin-7-one (5, 300 mg, 1.1 mmol) in toluene was added. Reaction mixture was degassed again and stirred at 100° C. under argon atmosphere for 20 h. Then it was cooled down to room temperature, and filtered through a layer of celite. Water (50 mL) and ethyl acetate (20 mL) were added to the filtrate solution and the two layers were separated by a separatory funnel. After the water layer was extracted by ethyl acetate two times, the combined organic layer was washed with water to make pH at 7, then brine, and dried over anhydrous Na$_2$SO$_4$. Filtration and removal of solvent gave the crude product, which was purified by Combiflash chromatography (10-30% of ethyl acetate in hexane) to yield the title compound (250 mg, 67.3%) as a light-yellow solid; mp 187-188° C. $^1$H NMR (300 MHz, DMSO-d$_6$): δ=9.05 (s, 1H), 8.29 (s, 1H), 7.653 (d, J=9.0 Hz, 1H), 7.652 (d, J=7.5 Hz, 1H), 7.54 (dd, J=7.5 Hz, 9.0 Hz, 1H), 2.62 (s, 3H).

6-(2,6-chlorophenyl)-2-(methylsulfonyl)-7H-pyrano [2,3-d]pyrimidin-7-one (10)

To a solution of 6-dichlorophenyl)-2-(methylthio)-7H-pyrano[2,3-d]pyrimidin-7-one (9, 300 mg, 0.89 mmol) in dichloromethane (7 mL), m-CPBA in dichloromethane (8 mL) was slowly added at room temperature. The reaction mixture was stirred and monitored by TLC. After 3 h, the reaction was stopped just by filtration and washing with diethyl ether. Pure title compound (301 mg, 91.4%) was obtained as a white solid; mp decomposistion at 245° C. $^1$H NMR (300M, DMSO-d$_6$): δ=9.46 (s, 1H), 8.48 (s, 1H), 7.686 (d, J=9.0 Hz, 1H), 7.684 (d, J=7.5 Hz, 1H), 7.58 (dd, J=7.5 Hz, 9.0 Hz, 1H), 3.48 (s, 3H). MS (EI): m/z=369.8 (M$^+$).

2-(4-Fluoro-3-methylphenylamino)-6-(2,6-dichlorophenyl)-7H-pyrano[2,3-d]pyrimidin-7-one (12a)

The mixture of 6-(2,6-dichlorophenyl)-2-(methylsulfonyl)-7H-pyrano[2,3-d]pyrimidin-7-one (197 mg, 0.53 mmol) and 4-fluoro-3-methylaniline (11a, 132.8 mg, 1.06 mmol) in DMF (6 mL) was heated to 110° C. and stirred overnight. Then the reaction mixture was cooled down to room temperature and quenched by adding water (60 mL). After the reaction mixture was extracted by ethyl acetate three times, the combined organic layer was washed by brine and then dried over anhydrous Na$_2$SO$_4$. Filtration and removal of solvent gave the crude product, which was purified by Combiflash chromatography (15-30% of ethyl acetate in hexane) to yield the title compound 12a (44 mg, 19.6%) as a light-yellow solid; mp 255-256° C. $^1$H NMR (300 MHz, chloroform-d): δ=8.60 (s, 1H), 7.58 (s, 1H), 7.55-7.40 (m, 5H), 7.303 (dd, J=7.5 Hz, 9.0 Hz, 1H), 7.02 (t, J=8.7 Hz, 1H), 2.32 (s, 3H). MS (EI): m/z=416.2 (M$^+$+1). Anal. Calcd for (C$_{20}$H$_{12}$Cl$_2$FN$_3$O$_2$): C, 57.71; H, 2.91; N, 10.10. Found: C, 57.79; H, 2.73; N, 9.97.

2-(3-(Methylthio)phenyl amino)-6-(2,6-dichlorophenyl)-7H-pyrano[2,3-d]pyrimidin-7-one (12b)

The mixture of 6-(2, 6-dichlorophenyl)-2-(methylsulfonyl)-7H-pyrano[2,3-d]pyrimidin-7-one (10, 200 mg, 0.54 mmol) and 3-(methylthio)aniline (11b, 150 mg, 1.08 mmol) in DMF (6 mL) was heated to 110° C. and stirred overnight. Then the reaction mixture was cooled down to room temperature and quenched by adding water (60 mL). After the reaction mixture was extracted by ethyl acetate three times, the combined organic layer was washed by brine and then dried over anhydrous Na$_2$SO$_4$. Filtration and removal of solvent gave the crude product, which was purified by Combiflash chromatography (10-30% of ethyl acetate in hexane) to yield the title compound (59 mg, 25.5%) as a yellow solid; mp 229-230° C. $^1$H NMR (300 MHz, chloroform-d): δ=8.63 (s, 1H), 7.66 (t, J=1.8 Hz, 1H), 7.59 (s, 1H), 7.57 (d, J=8.4 Hz, 1H), 7.47-7.39 (m, 3H), 7.35-7.27 (m, 2H), 7.04 (d, J=7.8 Hz, 1H), 2.53 (s, 3H). MS (EI): m/z=430.3 (M$^+$+1). Anal. Calcd for (C$_{20}$H$_{13}$Cl$_2$N$_3$O$_2$S): C, 55.82; H, 3.05; N, 9.77. Found: C, 55.71; H, 3.07; N, 9.53.

2-(3-Aminophenylamino)-6-(2,6-dichlorophenyl)-7H-pyrano[2,3-d]pyrimidin-7-one (12c)

A mixture of the sulfone 10 (700 mg, 1.88 mmol) and benzene-1,3-diamine (11c, 453 mg, 4.15 mmol) in diglyme (18.5 mL) was heated and stirred in a preheated oil bath at 150° C. for 1 h or till the complete consumption of the sulfone 10. The reaction mixture was cooled to rt. Then it was filtered through a celite padded funnel. The filtered residue was washed with EtOAc (20 mL). The filtrate was concentrated and the resultant crude product was purified by Combiflash chromatography (40%-90% ethyl acetate in hexane) and preparative TLC (30% ethyl acetate in hexane) to yield the product 10 (220.6 mg, 29.4%) as a white solid; mp 259-260° C. $^1$H NMR (500 MHz, DMSO-d6): δ 10.32 (brs, 1H), 8.87 (s, 1H), 8.12 (s, 1H), 7.63 (d, J=10 Hz, 2H), 7.52-7.49 (t, J=10 Hz, 5 Hz, 1H), 7.04-7.03 (t, J=5 Hz, 1H), 6.99-6.96 (t, J=10 Hz, 5 Hz, 1H), 6.88 (d, J=10 Hz, 1H), 6.31 (d, J=5 Hz, 1H), 5.41 (brs, 2H). $^{13}$C NMR (75 MHz, DMSO-d$_6$): δ 164.97, 160.27, 160.16, 158.09, 149.06, 142.69, 139.30, 134.93, 132.30, 132.30, 131.35, 128.92, 128.38, 118.72, 109.65, 108.47, 105.85. HRMS (ESI) m/z for $C_{19}H_{13}Cl_2N_4O_2$ [M +H]$^+$: calcd, 399.0416; found, 399.0414. Anal. Calcd for ($C_{19}H_{12}Cl_2N_4O_2$): C, 57.00; H, 2.75; N, 13.63. Found: C, 57.16; H, 3.03; N, 14.03.

3-(6-(2,6-Dichlorophenyl)-7-oxo-7H-pyrano[2,3-d]pyrimidin-2-ylamino)benzonitrile (12d)

The title compound was prepared from the sulfone 10 (300 mg, 0.81 mmol) and 3-aminobenzonitrile (11d, 191 mg, 1.62 mmol) in 18 mL diglyme according to the procedure described for the synthesis of 12c. The crude product was purified by Combiflash chromatography (0-60% ethyl acetate in hexane) to yield the product 12d (76 mg, 22.9%) as a light yellow solid; mp 276-278° C. $^1$H NMR (500 MHz, DMSO-d6): δ 10.88 (brs, 1H), 8.98 (s, 1H), 8.27 (t, J=5 Hz, 1H), 8.20 (s, 1H), 8.07-8.03 (m, 1H), 7.66-7.62 (m, 2H), 7.60-7.49 (m, 3H). $^{13}$C NMR (75 MHz, DMSO-d$_6$): δ 165.01, 160.63, 159.93, 157.99, 142.70, 140.06, 134.98, 132.23, 131.62, 130.38, 128.56, 126.60, 124.69, 124.59, 122.65, 120.14, 119.01, 111.72. FIRMS (ESI) m/z for ($C_{20}H_{11}Cl_2N_4O_2$) [M+H]$^+$ calcd, 409.0259; found, 409.0251. Anal. Calcd for ($C_{20}H_{10}Cl_2N_4O_2$): C, 58.70; H, 2.46; N, 13.69. Found: C, 58.44; H, 2.63; N, 13.47.

6-(2,6-Dichlorophenyl)-2-(3-methoxyphenylamino)-7H-pyrano[2,3-d]pyrimidin-7-one (12e)

The title compound was prepared from the sulfone 10 (250 mg, 0.67 mmol) and 3-methoxybenzenamine (11e, 182.5 mg, 1.48 mmol) in 8.3 mL diglyme (R$_f$=0.37, hexane:ethyl acetate=2:1) according to the procedure described for the synthesis of 12c. The crude product was purified by Combiflash chromatography (20-30% ethyl acetate in hexane) to obtain the product 12e (110 mg, 39.4%) as a white solid; mp 252-254° C. $^1$H NMR (500 MHz, DMSO-d$_6$): δ 10.53 (s, 1H), 8.92 (s, 1H), 8.15 (s, 1H), 7.64 (s, 1H), 7.62 (s, 1H), 7.53-7.50 (t, J=5.0 Hz, 1H), 7.49-7.48 (t, J=5.0 Hz, 1H), 7.36-7.35 (d, J=5.0 Hz, 1H), 7.28-7.26 (t, J=5.0 Hz, 1H), 6.69-6.67 (d, J=5.0 Hz, 1H), 3.77 (s, 1H). $^{13}$C NMR (75 MHz, DMSO-d$_6$): δ 165.36, 160.79, 160.46, 159.98, 158.39, 143.08 140.45, 135.33, 132.66, 131.83, 129.94, 128.83, 119.69, 113.00, 108.81, 106.71, 55.51. HRMS (ESI) m/z for $C_{20}H_{14}Cl_2N_3O_3$ [M+H]$^+$: calcd, 414.0412; found, 414.0408. Anal. Calcd for ($C_{20}H_{13}Cl_2N_3O_3$): C, 57.99; H, 3.16; N, 10.04. Found: C, 57.93; H, 2.94; N, 9.94.

6-(2,6-Dichlorophenyl)-2-(4-(dimethylamino)phenylamino)-7H-pyrano[2,3-d]pyrimidin-7-one (12f)

The title compound was prepared from the sulfone 10 (200 mg, 0.540 mmol) and N,N-dimethyl-p-phenylenediamine (11f, 110 mg, 0.810 mmol) in 12 mL diglyme (R$_f$=0.67, hexane:ethyl acetate=1:1) according to the procedure described for the synthesis of 12c. The crude product was purified by Combiflash chromatography (0-30% ethyl acetate in hexane) to yield the product 12f (145 mg, 62.8%) as a yellow solid; mp 276-278° C. $^1$H NMR (500 MHz, DMSO-d6): δ 10.29 (brs, 1H), 8.81 (s, 1H), 8.07 (s, 1H), 7.61 (d, J=5.0 Hz), 7.54-7.49 (m, 3H), 6.75 (d, J=15 Hz, 2H), 2.88 (s, 6H). $^{13}$C NMR (75 MHz, DMSO-d$_6$): δ 160.16, 158.13, 147.38, 142.75, 134.98, 132.40, 131.28, 128.36, 128.03, 122.13, 112.57, 40.46. HRMS (ESI) m/z for ($C_{21}H_{17}Cl_2N_4O_2$) [M+H]$^+$ calcd, 427.0729; found, 427.0724. Anal. calcd for ($C_{21}H_{16}Cl_2N_4O_2$): C, 59.03; H, 3.77; N, 13.11. Found: C, 59.09; H, 3.69; N, 12.97.

N-(3-(6-(2,6-Dichlorophenyl)-7-oxo-7H-pyrano[2,3-d]pyrimidin-2-ylamino)-phenyl)-acetamide (12 g)

The title compound was prepared from the sulfone 10 (301 mg, 0.81 mmol) and N-(3-aminophenyl)acetamide (11 g, 253.5 mg, 1.66 mmol) in 8.3 mL diglyme (R$_f$=0.27 hexane:ethyl acetate=1:2) according to the procedure described for the synthesis of 12c. The crude product was purified by Combiflash chromatography (40-100% ethyl acetate in hexane) to obtain the product 12 g (73.3 mg, 20.5%) as a white solid; mp 288-289° C. $^1$H NMR (500 MHz, DMSO-d6): δ 10.57 (s, 1H), 10.01 (s, 1H), 8.90 (s, 1H), 8.15 (s, 1H), 7.99 (s, 1H), 7.64 (s, 1H), 7.63 (s, 1H), 7.53-7.50 (t, J=5.0 Hz), 7.42-7.40 (m, 1H), 7.38-7.36 (m, 1H), 7.27-7.25 (t, J=5.0 Hz), 2.05 (s, 1H). $^{13}$C NMR (75 MHz, DMSO-d$_6$): δ 168.47, 165.11, 160.50, 160.26, 158.18, 142.80, 139.77, 139.16, 135.04, 132.38, 131.52, 128.90, 128.53, 124.73, 119.25, 115.58, 114.60, 111.41, 104.39, 24.19. HRMS (ESI) m/z for $C_{21}H_{15}Cl_2N_3O_3$ [M+H]$^+$: calcd, 414.0521; found, 414.0523.

6-Bromo-2-(methylsulfonyl)-7H-pyrano[2,3-d]pyrimidin-7-one (13)

6-Bromo-2-(methylsulfanyl)-7H-pyrano[2,3-d]pyrimidin-7-one (5, 500 mg) was dissolved in anhydrous DCM (30 mL) and stirred for 10 mins until it becomes a homogeneous solution. m-CPBA (906 mg, 77%) was added at 0° C. The reaction mixture was stirred at room temperature for 2 h. The reaction was monitored by TLC. After completion of the reaction, the precipitated solid was filtered and washed with cold ether (3×5 mL) and cold acetone (2 mL). The resultant compound was dried in vacuum oven to afford 320 mg of target compound. mp: 179-181° C. $^1$H NMR (300 MHz, CDCl$_3$): δ 9.33 (s, 1H), 8.75 (s, 1H), 3.48 (s, 3H).

tert-Butyl-4-(6-6-bromo-7-oxo-7H-pyrano[2,3-d]pyrimidin-2ylamino)pyridin-3-yl)piperazine-1-carboxylate (14)

The solution of 6-bromo-2-(methylsulfonyl)-7H-pyrano[2,3-d]pyrimidin-7-one (13, 100 mg) in DMF (2 mL) in a sealed tube was added K$_2$CO$_3$ (86 mg) with stirring for 5 mins. Then tert-butyl-4-(6-aminopyridin-3-yl)piperazine-1-carboxylate (109 mg) was added to the reaction mixture at room temperature. The reaction mixture in the sealed tube was heated in a preheated oil bath at 100° C. for 1 h. Upon the completion of the reaction, water (15 mL) was added and extracted organic compound with ethyl acetate (3×10 mL). The combined organic layer was washed with brine (15 mL) and then dried over sodium sulfate. Solvent was removed under reduced pressure to obtain the crude product, which was purified by Combiflash column chromatography (0-5% methanol in dichloromethane) to obtain the target compound (18 mg). $^1$H NMR (300 MHz, CDCl$_3$): δ 8.43 (d, J=3.0 Hz, 1H), 8.14 (d, J=3.0 Hz, 1H), 7.86 (d, J=3.0 Hz, 1H), 7.78 (d, J=9.0 Hz, 1H), 7.35-7.29 (m, 1H), 3.63 (t, J=4.9 Hz, 4H), 3.28 (t, J=4.9 Hz, 4H), 1.49 (s, 9H). MS (EI): m/z=502.0.

Example 2

Figure 4:
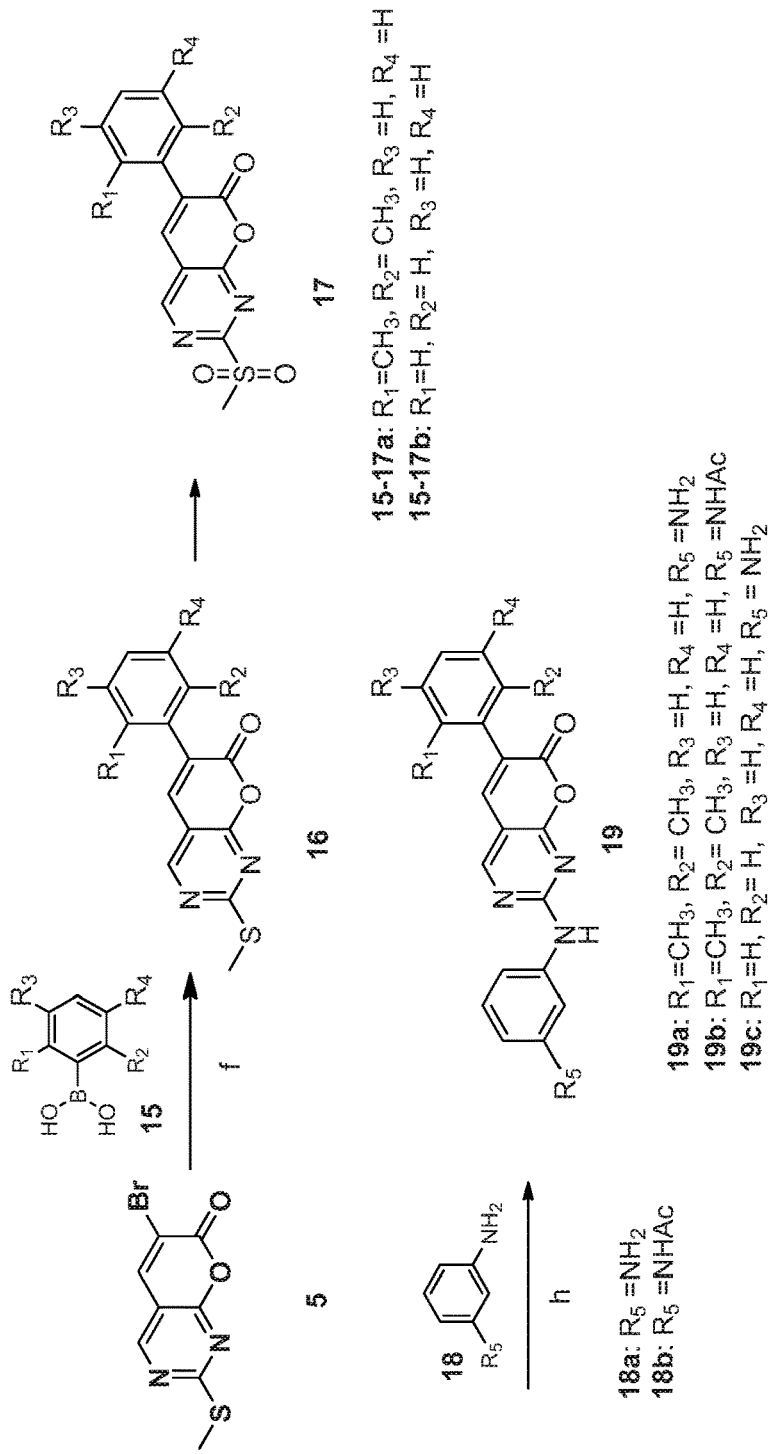

The syntheses described below are illustrated in FIG. 4.

6-(2,6-Dimethylphenyl)-2-(methylthio)-7H-pyrano[2,3-d]pyrimidin-7-one (16a)

To a 50 mL flask was added 6-bromo-2-(methylthio)-7H-pyrano[2,3-d]pyrimidin-7-one (5, 500 mg, 1.83 mmol), 2,6-dimethylphenylboronic acid (15a, 410 mg, 2.74 mmol), Pd$_2$(dba)$_3$ (167 mg, 0.18 mmol), SPhos (147 mg, 0.36 mmol), K$_3$PO$_4$ (1.16 g, 5.49 mmol) and dry toluene (10 mL). The resultant mixture was degassed with argon bubble for 2 minutes and stirred at 95° C. for 5 hours. The reaction mixture was cooled and filtered through a celite padded funnel. The cake was washed with EtOAc (200 mL) and the filtrate was washed with water (50 mL) and brine (20 mL). The organic layer was dried over anhydrous Na$_2$SO$_4$, filtered and concentrated. The residue was purified by Combiflash chromatography (10-30% EtOAc in hexane) to give the titled product 16a (295 mg, 54.0%) as a semisolid. (Rf=0.72 (Hexane/EtOAc=50/50)$^1$H NMR (300 MHz, CDCl$_3$) δ: 8.93 (s, 1H), 7.95 (s, 1H), 7.22 (m, 3H), 2.64 (s, 3H), 2.20 (s, 6H).

6-(2,6-Dimethylphenyl)-2-(methylsulfonyl)-7H-pyrano[2,3-d]pyrimidin-7-one (17a)

To a solution of 6-(2,6-dimethylphenyl)-2-(methylthio)-7H-pyrano[2,3-d]pyrimidin-7-one (16a, 285 mg, 0.95 mmol) in DCM (14 mL) was added m-CPBA (515 mg, 70%, 2.1 mmol) in portions at room temperature. The resulting mixture was stirred at room temperature for 3 hours. The precipitated solid was collected by filtration and washed with hexane. The solid crude product was dissolved in EtOAc (100 mL), washed with saturated aqueous NaHCO$_3$ solution (20 mL×2) and brine (20 mL). The organic layer was dried over anhydrous Na$_2$SO$_4$, filtered and concentrated to give the titled product (185 mg, 58.9%) as a yellow solid (Rf=0.42, Hexane/EtOAc=50/50). $^1$H NMR (300 MHz, CDCl$_3$) δ: 9.07 (s, 1H), 7.66 (s, 1H), 7.24 (m, 1H), 7.13 (m, 2H), 3.41 (s, 3H), 2.16 (s, 6H).

2-(3-Aminophenylamino)-6-(2,6-dimethylphenyl)-7H-pyrano[2,3-d]pyrimidin-7-one (19a)

To a suspension of 6-(2,6-dimethylphenyl)-2-(methylsulfonyl)-7H-pyrano[2,3-d]pyrimidin-7-one (17a, 90 mg, 0.27 mmol) in diglyme (2.4 mL) was added m-phenylenediamine (18a, 63 mg, 0.59 mmol). The resulting mixture was stirred at 150° C. under argon atmosphere for 1 hour. The reaction mixture was cooled, filtered through a celite padded funnel. The cake was washed with EtOAc (10 mL). The filtrate was concentrated and the resultant crude product was purified by preparative TLC (DCM/MeOH=10/1) to give the titled product (22 mg, 22.7%) as a yellow solid (R$_f$=0.59, DCM/MeOH=10/1). $^1$H NMR (300 MHz, CDCl$_3$) δ: 8.59 (s, 1H), 7.56 (s, 1H), 7.46 (s, 1H), 7.36 (s, 1H), 7.21 (m, 1H), 7.15 (m, 3H), 6.90 (d, 1H, J=7.8 Hz), 6.49 (d, 1H, J=7.8 Hz), 2.21 (s, 6H). mp 223-226° C. LRMS (ESI) m/z for C$_{21}$H$_{18}$N$_4$O$_2$ [M+H]$^+$: calcd, 358.1430; found, 359.1.

N-(3-(6-(2,6-Dimethylphenyl)-7-oxo-7H-pyrano[2,3-d]pyrimidin-2-ylamino)phenyl)-acetamide (19b)

To a suspension of 6-(2,6-dimethylphenyl)-2-(methylsulfonyl)-7H-pyrano[2,3-d]pyrimidin-7-one (17a, 90 mg, 0.27 mmol) in diglyme (2.4 mL) was added N-(3-aminophenyl)acetamide (18b, 88 mg, 0.6 mmol). The resulting mixture was heated and stirred at 150° C. under argon atmosphere for 1.5 hours. The reaction mixture was cooled, filtered through a celite padded funnel. The cake was washed with EtOAc (5 mL). The filtrate was concentrated and the residue was purified by Combiflash (10-70% EtOAc in hexane) to give the titled product (40 mg, 37.9%) as a yellow solid (R$_f$=0.50, hexane/EtOAc=1:3). $^1$H NMR (300 MHz, CDCl$_3$) δ: 9.36 (s, 1H), 8.81 (s, 1H), 8.17 (s, 1H), 7.83 (s, 1H), 7.54 (t, 2H, J=9.9 Hz), 7.29 (t, 1H, J=8.1 Hz), 7.23-7.11 (m, 3H), 2.20 (s, 6H), 2.10 (s, 3H). mp 252-254° C. HRMS (ESI) m/z for C$_{23}$H$_{20}$N$_4$O$_3$ [M+H]$^+$: calcd, 401.1614; found, 401.1609.

2-(Methylthio)-6-phenyl-7H-pyrano[2,3-d]pyrimidin-7-one (16b)

To a 50 mL flask was added 6-bromo-2-(methylthio)-7H-pyrano[2,3-d]pyrimidin-7-one (5, 1.36 g, 5 mmol), phenylboronic acid (914 mg, 7.5 mmol), Pd$_2$(dba)$_3$ (457 mg, 0.5 mmol), SPhos (410 mg, 1 mmol), K$_3$PO$_4$ (3.18 g, 15 mmol) and dry toluene (25 mL). The resulting suspension was degassed with argon for 2 minutes and stirred at 95° C. for 5 hours. The reaction mixture was cooled to room temperature and the solids were removed by filtration. The filtrate was concentrated and the residue was purified by Combiflash chromatography (10-50% of EtOAc in hexane) and ether (50 mL) trituration to give the titled product 16b (860 mg, 63.7%) as a yellow solid. (Rf=0.50, Hexane/EtOAc=50/50) $^1$H NMR (300 MHz, DMSO-d$_6$) δ: 8.99 (s, 1H), 8.26 (s, 1H), 7.69 (m, 2H), 7.47 (m, 3H), 2.60 (s, 3H).

2-(Methyl sulfonyl)-6-phenyl-7H-pyrano[2,3-d]pyrimidin-7-one (17b)

To a solution of 2-(methylthio)-6-phenyl-7H-pyrano[2,3-d]pyrimidin-7-one (16b, 860 mg, 3.18 mmol) in DCM (20 mL) was added m-CPBA (1.73 g, 70%, 7.0 mmol) in portions at room temperature. The resulting mixture was stirred at room temperature for 5 hours. The precipitated solid was collected by filtration, washed with DCM (20 mL) and ether (20 mL), and dried under vacuum to give the titled product 17b (410 mg, 42.7%) as a pale yellow solid. (Rf=0.25, Hexane/EtOAc=50/50). $^1$H NMR (300 MHz, DMSO-d$_6$) δ: 9.39 (s, 1H), 8.41 (s, 1H), 7.76 (m, 2H), 7.52 (m, 3H), 3.48 (s, 3H).

2-(3-Aminophenylamino)-6-phenyl-7H-pyrano[2,3-d]pyrimidin-7-one (19c)

To a suspension of 2-(methylsulfonyl)-6-phenyl-7H-pyrano[2,3-d]pyrimidin-7-one (17b, 100 mg, 0.33 mmol) in diglyme (2.4 mL) was added m-phenylenediamine (78.5 mg, 0.73 mmol). The resulting mixture was stirred at 150° C. for 1 hour under argon atmosphere. The reaction mixture was cooled to room temperature and filtered. The filtrate was concentrated and the residue was purified by Combiflash chromatography (5-50% of EtOAc in hexane) to give the titled product 19c (17 mg, 15.6%) as a yellow solid. (Rf=0.55, Hexane/EtOAc=50/50). $^1$H NMR (300 MHz, DMSO-d$_6$) δ: 10.15 (s, 1H), 8.84 (s, 1H), 8.18 (s, 1H), 7.68

(d, 2H, J=6.9 Hz), 7.44 (m, 3H), 7.05 (s, 1H), 6.94 (m, 2H), 6.28 (d, 1H, J=7.8 Hz), 5.11 (s, 2H).

Example 3

Figure 5:
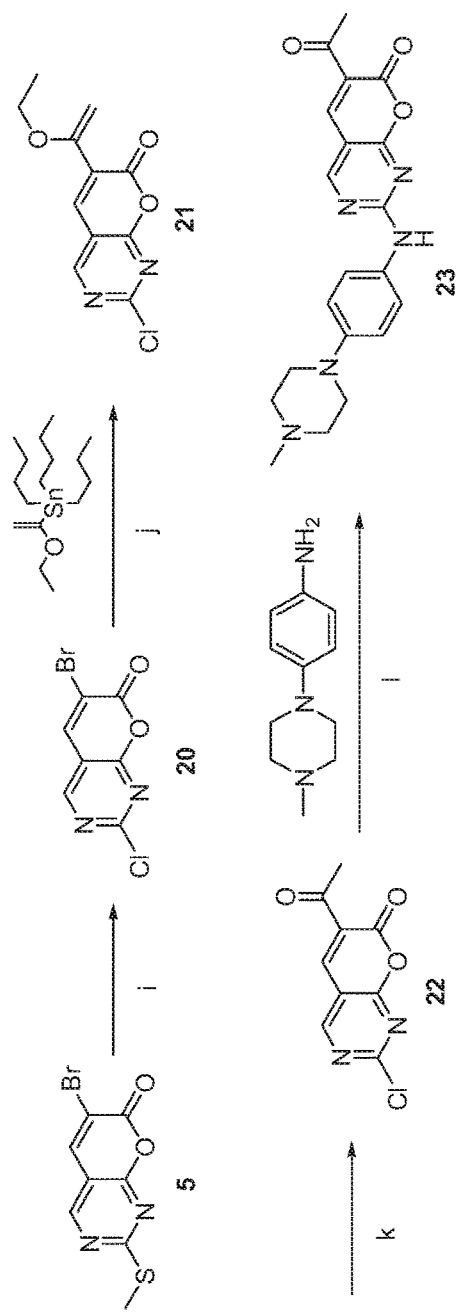
Figure 6:
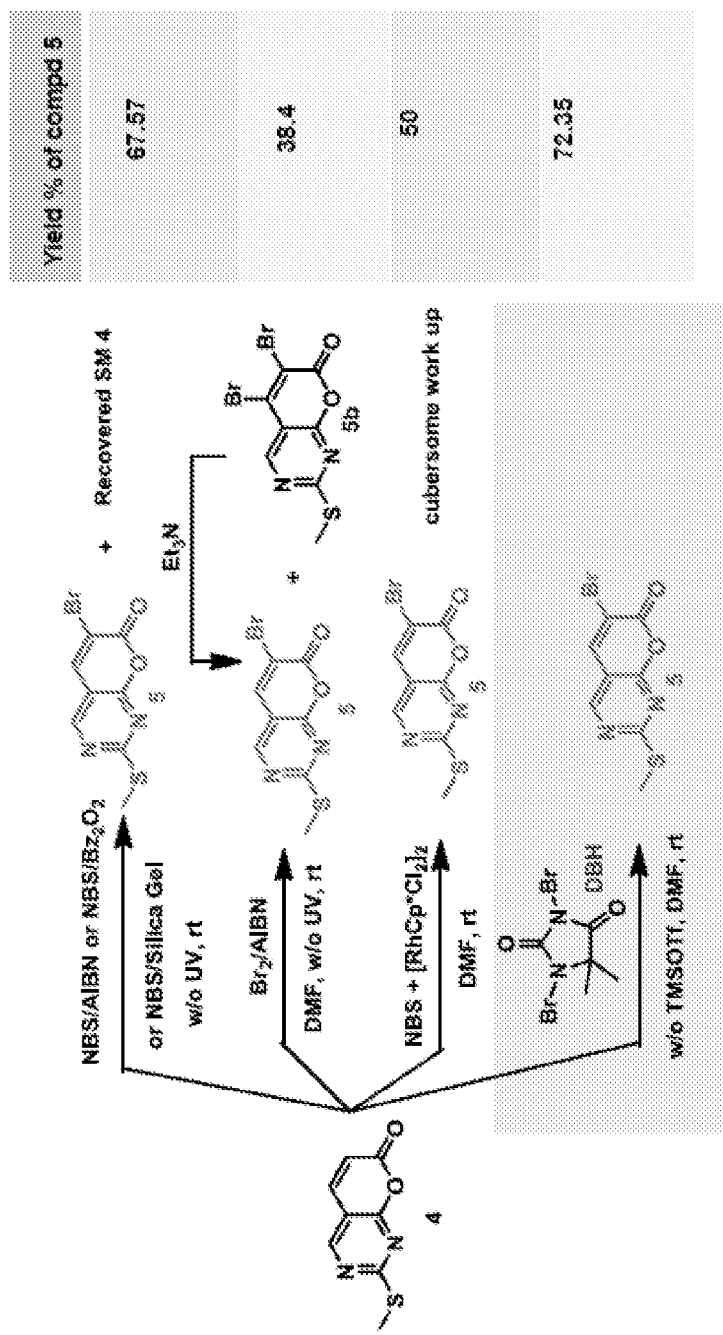
FIG. 6 is a schematic illustration of the synthetic routes for optimization of bromination of 4 to achieve the desired intermediate 5.
Figure 7:
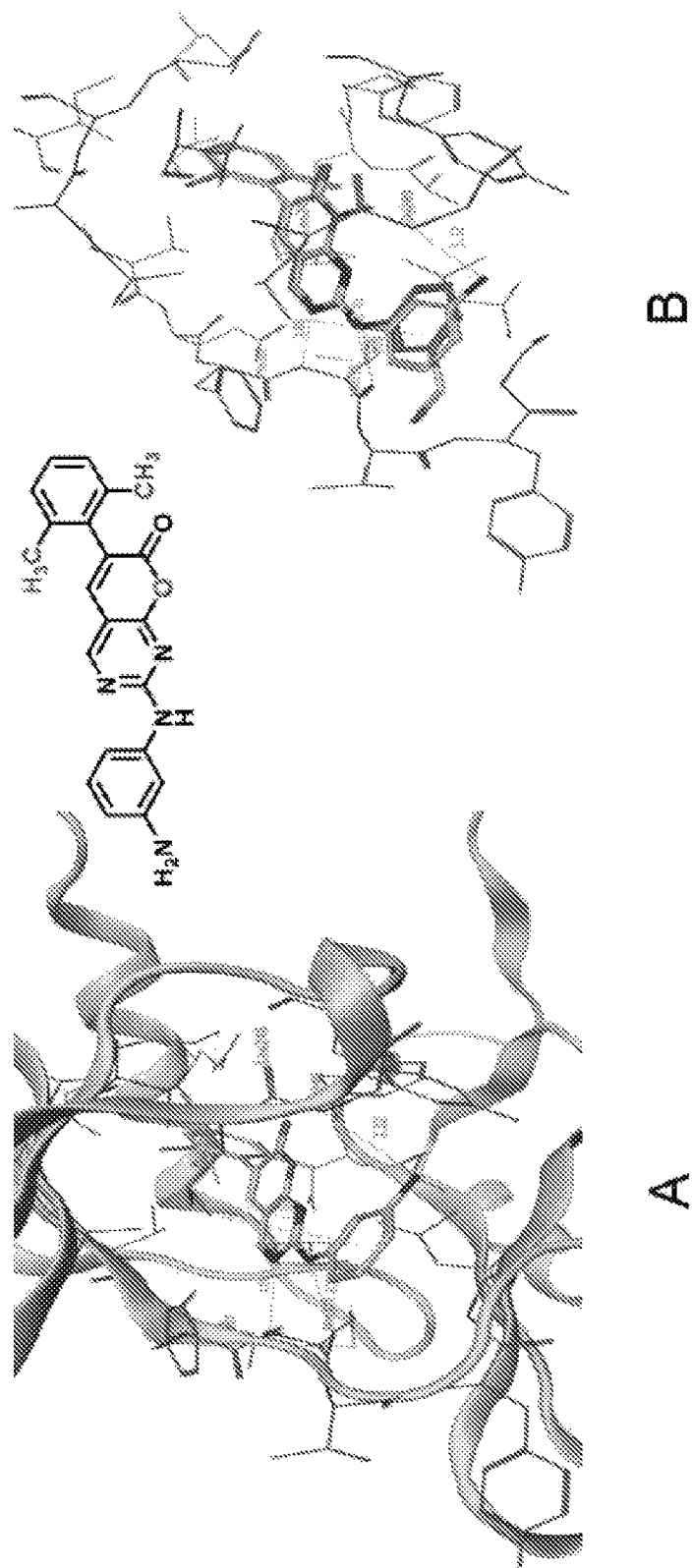
FIGS. 7A and 7B depict Compound 19a bound in its binding site of c-Abl (7A) and PD173955 and Compound IX superimposed in the binding site of c-Abl (7B).
Figure 8:
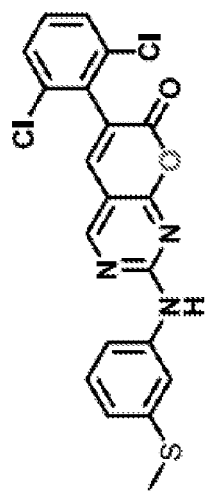
FIGS. 8A and 8B depict PD173955 and Compound 12e bound in the binding site of c-Abl, respectively.
Figure 8:
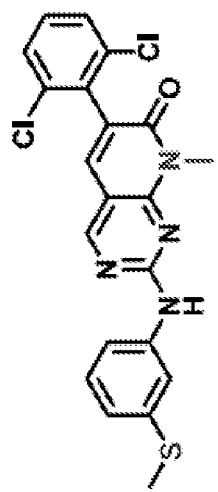
Figure 8:
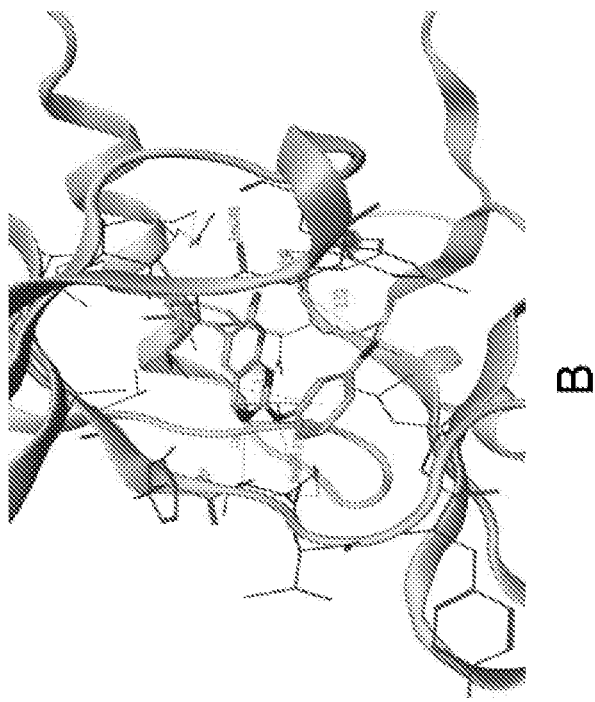
Figure 8:

The syntheses described below are illustrated in FIG. 5.

6-Bromo-2-chloro-7H-pyrano[2,3-d]pyrimidin-7-one (20)

To a solution of 6-bromo-2-(methylthio)-7H-pyrano[2,3-d]pyrimidin-7-one (5, 2.4 g, 8.7 mmol) in anhydrous acetonitrile (5.4 mL) was added $SO_2Cl_2$ (8.3 mL, 86.8 mmol) dropwise at room temperature. The resulting mixture was stirred and refluxed for 2 hours and then cooled to room temperature. The reaction mixture was concentrated under reduced pressure and the residue was dissolved in EtOAc (100 mL). The solution was washed with saturated $NaHCO_3$ (50 mL×2), water and brine. The organic layer was dried over anhydrous $Na_2SO_4$, filtered and concentrated. The residue was triturated with hexane (30 mL) to provide the titled product (1.8 g, 83.3%) as a white solid. $R_f$=0.32, hexane/EtOAc=2/1. mp 225-226° C. $^1$H NMR (300 MHz, DMSO-$d_6$): δ 9.06 (s, 1H), 8.67 (s, 1H). MS (ESI) m/z for $C_7H_3BrClN_2O_2$ [M+H]$^+$: calcd, 260.9; found, 260.9; [M+H+2]$^+$: 262.9; found, 262.9.

2-Chloro-6-(1-ethoxyvinyl)-7H-pyrano[2,3-d]pyrimidin-7-one (21)

To a solution of 6-bromo-2-chloro-7H-pyrano [2, 3-d] pyrimidin-7-one (20, 2.1 g, 8.0 mmol) in 1,4-dioxane (20 mL) was added 1-ethoxyvinyltributyltin (2.8 mL, 8.0 mmol) and Pd(PPh$_3$)$_4$. The resulting mixture was degassed with argon for 3 minutes and stirred and refluxed for 2 hours. The reaction mixture was cooled to room temperature and filtered through a pad of celite. The filtrate was concentrated and the residue was purified by Comiflash chromatography (0-20% of EtOAc in hexane) to give the titled product (831.4 mg, 41.1%). $R_f$=0.63 (hexane/EtOAc=2/1). mp 190-192° C. $^1$H NMR (300 MHz, CDCl$_3$): δ 8.85 (s, 1H), 8.17 (s, 1H), 5.81 (d, J=2.8 Hz, 1H), 4.74 (d, J=2.8 Hz, 1H), 3.96 (q, J=7.0 Hz, 2H), 1.47 (t, J=7.0 Hz, 3H). MS (APCI) m/z for $C_{11}H_8ClN_2O_3$ [M−H]$^-$: calcd, 251.1; found, 251.1; [M−H+2]$^-$: calcd, 253.0; found, 253.1.

6-Acetyl-2-chloro-7H-pyrano[2,3-d]pyrimidin-7-one (22)

To a solution of 2-chloro-6-(1-ethoxyvinyl)-7H-pyrano[2,3-d]pyrimidin-7-one (21, 916.8 mg, 3.6 mmol) in 1,4-dioxane (7.2 mL) was added aqueous HCl solution (2N, 9.0 mL, 18 mmol) at room temperature. The resulting solution was stirred at room temperature for 30 minutes and concentrated. The residue was partitioned with EtOAc (50 mL) and saturated $NaHCO_3$ solution (20 mL). The organic layer was dried over anhydrous $Na_2SO_4$. Filtration and concentration provided the titled product (753.1 mg, 92.4%) as an off-white solid. $R_f$=0.26 (hexane/EtOAc=2/1). mp 171-173° C. $^1$H NMR (300 MHz, CDCl$_3$): δ 8.94 (s, 1H), 8.51 (s, 1H), 2.73 (s, 1H). MS (APCI) m/z for $C_9H_6ClN_2O_3$ [M+H]$^+$: calcd, 225.0; found, 224.8; [M+H+2]$^+$: calcd, 227.0; found, 226.8.

2-(4-(4-Methylpiperazin-1-yl)phenylamino)-6-acetyl-7H-pyrano[2,3-d]pyrimidin-7-one (23)

To a solution of 6-acetyl-2-chloro-7H-pyrano[2,3-d]pyrimidin-7-one (22, 200 mg, 0.9 mmol) in 2-butanol (7.2 mL) was added 4-(4-methyl-piperazino)aniline (176 mg, 0.9 mmol) and TFA (66 μL, 0.9 mmol). The resulting mixture was stirred at reflux overnight and then cooled to room temperature. The reaction mixture was concentrated and the residue was partitioned with EtOAc (200 mL) and saturated aqueous $NaHCO_3$ solution (20 mL). The organic layer was washed with water, brine, dried over anhydrous $Na_2SO_4$, filtered and concentrated. The resultant residue was purified by Combiflash chromatography (DCM/MeOH/Et$_3$N=1000/100/1) to give the titled product (99 mg, 29.2%) as a red solid. $R_f$=0.24 (hexane/EtOAc/Et$_3$N=100:300:1). Mp >240° C. $^1$H NMR (300 MHz, DMSO-$d_6$): δ 10.63 (brs, 1H), 8.96 (s, 1H), 8.60 (s, 1H), 7.56 (d, J=8.1 Hz), 6.94 (d, J=8.1 Hz), 3.11 (t, J=4.6 Hz, 4H), 2.53 (s, 3H), 2.45 (t, J=4.6 Hz, 4H), 2.22 (s, 3H). FIRMS (ESI) m/z for ($C_{20}H_{22}N_5O_3$) [M+H]$^+$ calcd, 380.1723; found, 380.1721. Anal. Calcd for ($C_{20}H_{21}N_5O_3H_2O$): C, 60.44; H, 5.83; N, 17.62. Found: C, 60.60; H, 5.56; N, 17.34.

Example 4

The pharmacological activities of some invented compounds as protein kinase modulators are illustrated in TABLE 1.

TABLE 1

Biological activities of selected compounds against Abelson kinase 1 (ABL1)

| Compound | Structure | $K_d$ (nM)$^a$ | $IC_{50}$ (nM)$^b$ |
|---|---|---|---|
| PD173955 | 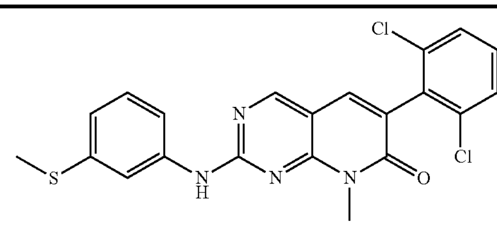 | 0.58 | Lit$^c$ |
| 12a | 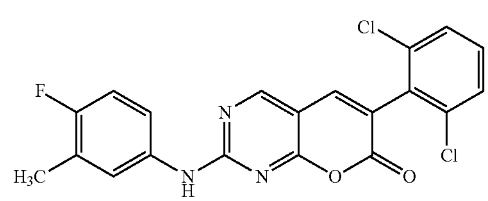 [SMILES: Cc1cc(Nc2ncc3cc(-c4c(Cl)cccc4Cl)c(=O)oc3n2)ccc1F] | 3.5 | 17.5 |

TABLE 1-continued

Biological activities of selected compounds against Abelson kinase 1 (ABL1)

| Compound | Structure | $K_d$ (nM)[a] | $IC_{50}$ (nM)[b] |
|---|---|---|---|
| 12b | 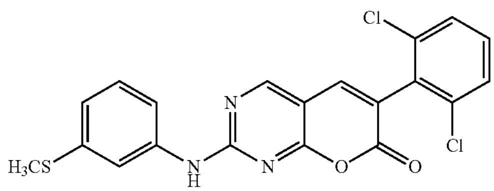 | 3.3 | 18.7 |
| 12c | 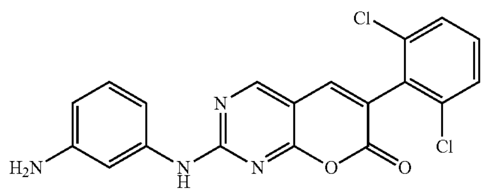 [SMILES: Nc1cccc(Nc2ncc3cc(-c4c(Cl)cccc4Cl)c(=O)oc3n2)c1] | 0.4 | 2.13 |
| 12d | 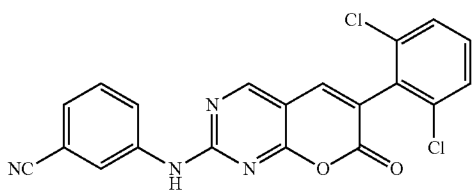 [SMILES: N#Cc1cccc(Nc2ncc3cc(-c4c(Cl)cccc4Cl)c(=O)oc3n2)c1] | 2.6 | 42.6 |
| 12e | 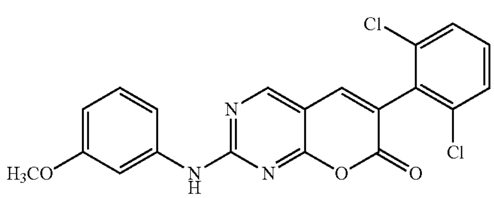 [SMILES: COc1cccc(Nc2ncc3cc(-c4c(Cl)cccc4Cl)c(=O)oc3n2)c1] | 1.5 | 16.1 |
| 12f | 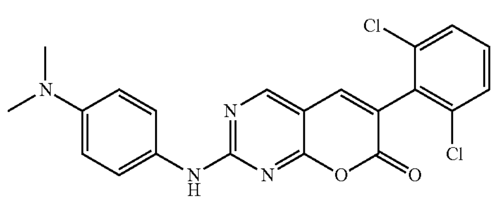 [SMILES: CN(C)c1ccc(Nc2ncc3cc(-c4c(Cl)cccc4Cl)c(=O)oc3n2)cc1] | 1.5 | 15.7 |
| 12g | 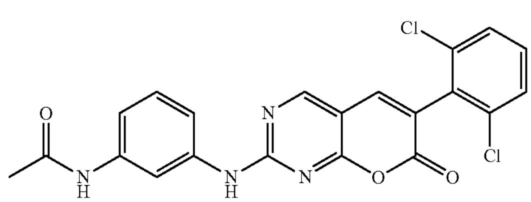 [SMILES: CC(=O)Nc1cccc(Nc2ncc3cc(-c4c(Cl)cccc4Cl)c(=O)oc3n2)c1] | 0.91 | 3.51 |
| 19a | 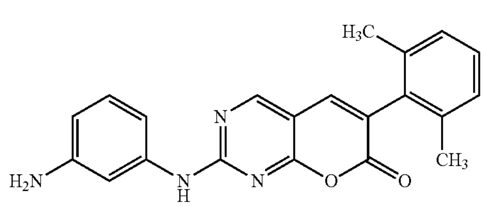 [SMILES: Cc1cccc(C)c1-c1cc2cnc(Nc3cccc(N)c3)nc2oc1=O] | 0.38 | 1.27 |

TABLE 1-continued

Biological activities of selected compounds against Abelson kinase 1 (ABL1)

| Compound | Structure | $K_d$ (nM)[a] | $IC_{50}$ (nM)[b] |
|---|---|---|---|
| 19b | 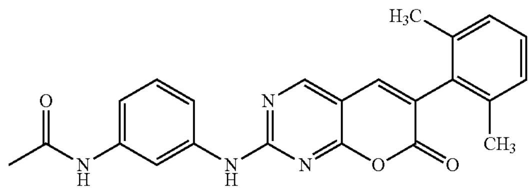 [SMILES: CC(=O)Nc1cccc(Nc2ncc3cc(-c4c(C)cccc4C)c(=O)oc3n2)c1] | 0.66 | 2.09 |

[a]$K_d$ for Abelson kinase ABL1 was determined by DiscoverX corporation though the KINOMEscan™ competition binding assay (https://www.discoverx.com/kinase-data-sheets/abl1-nonphosphorylated).
[b]$IC_{50}$ against Abelson kinase ABL1 was determined by Life Technologies corporation though the Z'-LITE biochemical assay.
[c]See Wang, J.; Pendergast, A.M. *Trans Cancer*, 2015, 1, 110-123 and Nagar, B.; et al; *Cancer Res*, 2002, 62, 4236-4243.

While the preferred embodiments of the invention have been illustrated and described, it will be appreciated that various changes can be made therein without departing from the spirit and scope of the invention.

The invention claimed is:

1. A compound of Formula (A):

(A)

or a pharmaceutically acceptable salt thereof, wherein
Z is selected from the group consisting of hydrogen, halogen, C(halogen)$_3$, a $C_1$-$C_6$ alkyl, and $C_3$-$C_6$ cycloalkyl;
$X^1$ is selected from the group consisting of $NH_2$, $NR^1$, O, and S, wherein when $X^1$ is O, R—$(X^3)_r$—$(X^2)_q$-is not methyl;
$R^1$ is selected from the group consisting of hydrogen, $C_1$-$C_6$ alkyl, and $C_3$-$C_6$ cycloalkyl;
$X^2$ is an optionally substituted aryl or optionally substituted heteroaryl;
$X^3$ is an optionally substituted heterocyclyl;
R is hydrogen or alkyl;
$Y^1$ is O or an optionally substituted group selected from the group consisting of an aryl, a heteroaryl, an alkenyl, an alkynyl, and an acyl group;
$Y^2$ is an optionally substituted heteroaryl;
$S^1$ is hydrogen, halogen, alkyl, alkoxyl, cycloalkyl, cyano, OH, $SQ^1$, acyl, haloalkyl, heteroaryl, C(halogen)$_3$, CN, C(=O)CH$_3$, NQ$^1$C(=O)Q$^2$, C(=O)NQ$^1$Q$^2$, N$_3$, NCS, NO$_2$, or NQ$^1$Q$^2$, wherein Q$^1$ and Q$^2$ are independently selected from hydrogen and alkyl;
m is 0 or 1;
n is 0 or 1;
p is 1;
q is 0 or 1; and
r is 0 or 1.

2. The compound of claim 1, wherein the compound of formula (A) has the structure of Formula (A1):

(A1)

or a pharmaceutically acceptable salt thereof, wherein
Z is selected from the group consisting of hydrogen, halogen, CF$_3$, CCl$_3$, $C_1$-$C_6$ alkyl, and $C_3$-$C_6$ cycloalkyl;
$X^1$ is selected from the group consisting of NR$^1$, O, and S;
Ar$^1$ is an optionally substituted aryl or optionally substituted heteroaryl;
Ar$^2$ is an optionally substituted aryl or optionally substituted heteroaryl; and
R$^1$ is hydrogen, $C_1$-$C_6$ alkyl or $C_3$-$C_6$ cycloalkyl.

3. The compound of claim 1, wherein $X^1$ is NR$^1$.

4. The compound of claim 3, wherein the compound has the structure of Formula (A2):

(A2)

or a pharmaceutically acceptable salt thereof, wherein
R$^X$ is hydrogen, halogen, alkyl, alkoxyl, cycloalkyl, cyano, OH, SQ$^1$, acyl, haloalkyl, heteroaryl, C(halogen)$_3$, CN, C(=O)CH$_3$, NQ$^1$C(=O)Q$^2$, C(=O)NQ$^1$Q$^2$, N$_3$, NCS, NO$_2$, or NQ$^1$Q$^2$, wherein Q$^1$ and Q$^2$ are independently selected from H and $C_1$-$C_{10}$ alkyl; and
x is 0, 1, 2, 3, 4, or 5.

5. The compound of claim 4, wherein the compound has the structure of Formula (A3):

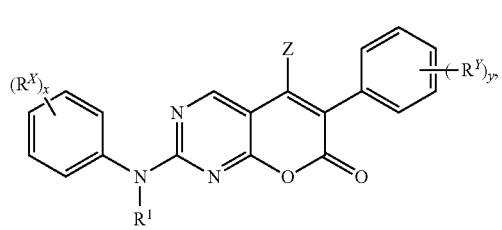

(A3)

or a pharmaceutically acceptable salt thereof, wherein
$R^Y$ is hydrogen, halogen, alkyl, alkoxyl, cycloalkyl, cyano, OH, $SQ^1$, acyl, haloalkyl, heteroaryl, C(halogen)$_3$, CN, C(=O)CH$_3$, NQ$^1$C(=O)Q$^2$, C(=O)NQ$^1$Q$^2$, N$_3$, NCS, NO$_2$, or NQ$^1$Q$^2$, wherein Q$^1$ and Q$^2$ are independently selected from H and C$_1$-C$_{10}$ alkyl; and y is 0, 1, 2, 3, 4, or 5.

6. The compound of claim 5, wherein R$^1$ is hydrogen or methyl.

7. The compound of claim 4, wherein Z is hydrogen, halogen, or methyl.

8. The compound of claim 4, wherein the compound has the structure of Formula (A4):

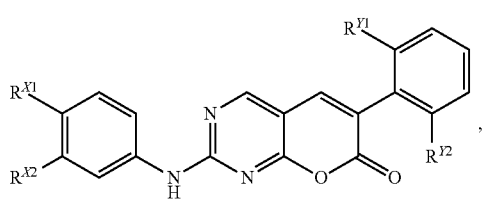

(A4)

or a pharmaceutically acceptable salt thereof, wherein
$R^{X1}$, $R^{X2}$, $R^{Y1}$, and $R^{Y2}$ are independently selected from the group consisting of hydrogen, halogen, alkyl, alkoxyl, cycloalkyl, cyano, OH, SQ$^1$, acyl, haloalkyl, heteroaryl, C(halogen)$_3$, CN, C(=O)CH$_3$, NQ$^1$C(=O)Q$^2$, C(=O)NQ$^1$Q$^2$, N$_3$, NCS, NO$_2$, and NQ$^1$Q$^2$, wherein Q$^1$ and Q$^2$ are independently selected from H and C$_1$-C$_{10}$ alkyl.

9. The compound of claim 8, wherein R$^{Y1}$ and R$^{Y2}$ are independently selected from H, F, Cl, and CH$_3$.

10. The compound of claim 8, wherein R$^{X1}$ is selected from H, F, Cl, N(CH$_3$)$_2$, and CH$_3$.

11. The compound of claim 8, wherein R$^{X2}$ is selected from NH$_2$, OCH$_3$, CN, SCH$_3$, NHC(O)CH$_3$, and CH$_3$.

12. The compound of claim 1, or a pharmaceutically acceptable salt thereof, wherein the compound is Compound 12a, 12b, 12c, 12d, 12e, 12f, 12g, 19a, or 19b:

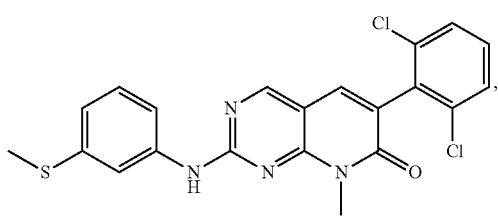

(12a)

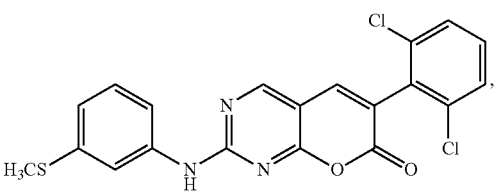

(12b)

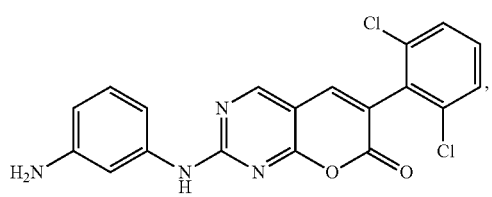

(12c)

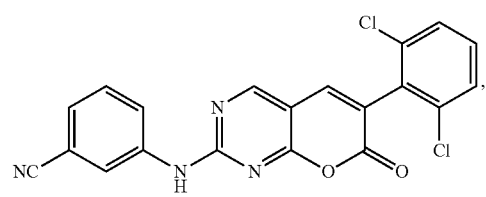

(12d)

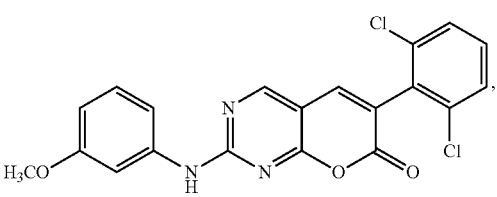

(12e)

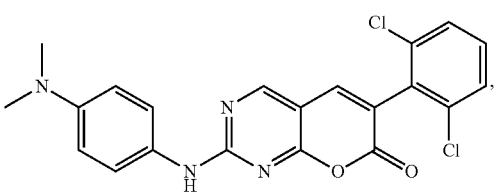

(12f)

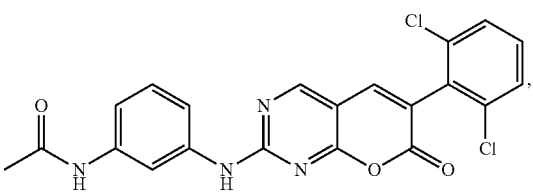

(12g)

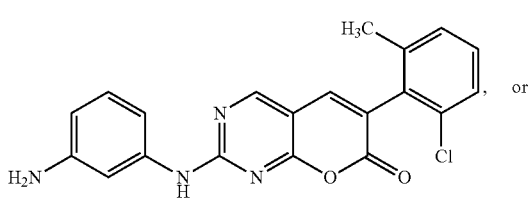

(19a) or (19b)

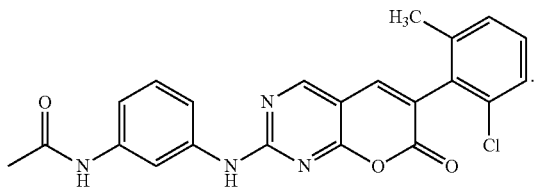

13. A pharmaceutical composition comprising a compound of claim 1, or a pharmaceutically acceptable salt thereof, and a pharmaceutically acceptable carrier.

14. A method of making a 2-alkylsulfanylpyrano[2,3-d]pyrimidin-7-one comprising:
(i) contacting 2-alkylthiourea hemihydrate with a coumalate ester in a suitable solvent in the presence of a suitable base, thereby forming a 3-(2-alkylsulfanyl-6-oxo-1,6-dihydro-pyrimidin-5-yl)acrylic acid; and
(ii) contacting the 3-(2-alkylsulfanyl-6-oxo-1,6-dihydro-pyrimidin-5-yl)acrylic acid of step (i) with an anhydride thereby forming the 2-alkylsulfanylpyrano[2,3-d]pyrimidin-7-one.

15. The method of claim 14, wherein 2-alkylthiourea hemihydrate is 2-methylthiourea hemihydrate.

16. A method of making 6-bromo-2-(methylthio)-7H-pyrano [2,3-d] pyrimidin-7-one comprising contacting 2-methylsulfanylpyrano [2,3-d] pyrimidin-7-one with 1,3-dibromo-5,5-dimethylhydantoin (DBDMH) in a suitable solvent wherein the contacting results in 6-bromo-2-(methylthio)-7H-pyrano [2,3-d] pyrimidin-7-one.

17. The method of claim 16, wherein the solvent is DMF.

* * * * *

UNITED STATES PATENT AND TRADEMARK OFFICE
CERTIFICATE OF CORRECTION

PATENT NO. : 11,136,333 B2
APPLICATION NO. : 16/304073
DATED : October 5, 2021
INVENTOR(S) : D. Lu et al.

It is certified that error appears in the above-identified patent and that said Letters Patent is hereby corrected as shown below:

In the Claims

| Column | Line | |
|---|---|---|
| 26 & 27 | 7 & 1 | Claim 12, change "Cl" to --$CH_3$--. |

Signed and Sealed this
Thirtieth Day of August, 2022

Katherine Kelly Vidal
*Director of the United States Patent and Trademark Office*